United States Patent
Jung et al.

(10) Patent No.: US 7,655,155 B2
(45) Date of Patent: Feb. 2, 2010

(54) LIQUID CRYSTAL THERMOSET MONOMER OR OLIGOMER, THERMOSETTING LIQUID CRYSTAL POLYMER COMPOSITION COMPRISING THE SAME AND PRINTED CIRCUIT BOARD USING THE SAME

(75) Inventors: Myung Sup Jung, Seongnam-si (KR); Chung Kun Cho, Suwon-si (KR); Yong Ho Ahn, Uiwang-si (KR); Seo Won Jang, Daejeon (KR); Jin Hae Chang, Seoul (KR); Mahn Jong Kim, Daejeon (KR); Chung Won Park, Daejeon (KR)

(73) Assignees: Samsung Electronics Co., Ltd. (KR); Samsung Electro-Mechanics Co., Ltd. (KR); Samsung Fine Chemicals Co., Ltd. (KR)

( * ) Notice: Subject to any disclaimer, the term of this patent is extended or adjusted under 35 U.S.C. 154(b) by 8 days.

(21) Appl. No.: 12/173,237

(22) Filed: Jul. 15, 2008

(65) Prior Publication Data
US 2009/0224203 A1    Sep. 10, 2009

(30) Foreign Application Priority Data
Mar. 5, 2008    (KR) ...................... 10-2008-0020557

(51) Int. Cl.
*C09K 19/38* (2006.01)
*C09K 19/34* (2006.01)
*C09K 19/32* (2006.01)
*C09K 19/20* (2006.01)
*C07D 207/452* (2006.01)
*C08G 73/14* (2006.01)
*C08G 73/16* (2006.01)
*C08F 126/06* (2006.01)

(52) U.S. Cl. ............................ 252/299.01; 252/299.61; 252/299.62; 252/299.66; 252/299.67; 548/521; 548/548; 526/262; 528/322

(58) Field of Classification Search ............ 252/299.61, 252/299.62, 299.66, 299.67; 548/521, 548; 528/322; 526/262
See application file for complete search history.

(56) References Cited

U.S. PATENT DOCUMENTS 4,876,358 A * 10/1989 Alexander .................. 548/521
6,169,186 B1 * 1/2001 Imai et al. .................. 548/521

* cited by examiner

*Primary Examiner*—Shean C Wu
(74) *Attorney, Agent, or Firm*—Cantor Colburn LLP

(57) ABSTRACT

A liquid crystal thermoset (LCT) monomer or oligomer having both ends capped with maleimide having at least one methyl group, represented by Formula 1:

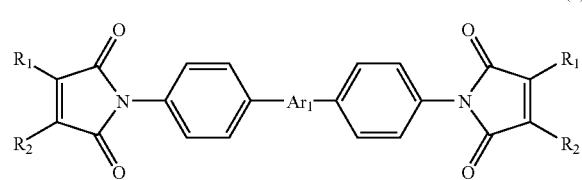

(1)

wherein $R_1$ and $R_2$ are each independently $CH_3$ or H, and at least one of $R_1$ and $R_2$ is a methyl group, and $Ar_1$ is a divalent organic group containing one or more structural units selected from the group consisting of ester, amide, ester amide, ester imide and ether imide units, and $Ar_1$ has a molecular weight not greater than 5,000.

17 Claims, 6 Drawing Sheets

LIQUID CRYSTAL THERMOSET MONOMER OR OLIGOMER, THERMOSETTING LIQUID CRYSTAL POLYMER COMPOSITION COMPRISING THE SAME AND PRINTED CIRCUIT BOARD USING THE SAME

This application claims priority to Korean Patent Application No. 10-2008-0020557, filed on Mar. 5, 2008, and all the benefits accruing there from under 35 U.S.C. §119, the contents of which in their entirety are herein incorporated by reference.

BACKGROUND OF THE INVENTION

1. Field of the Invention

This disclosure is directed to a liquid crystal thermoset ("LCT") monomer or oligomer, a thermosetting liquid crystal polymer composition including the LCT monomer or oligomer, and a printed circuit board using the LCT monomer or oligomer. More specifically, the LCT monomer or oligomer is terminated with methylmaleimide. The presence of the terminal methylmaleimide in the LCT monomer or oligomer allows for the production of a printed circuit board with excellent characteristics in terms of flame retardancy, heat resistance and mechanical properties.

2. Description of the Related Art

Recent advances in information and communication technologies have transformed our society into a high-tech communication and information society. The trend toward miniaturization and high performance of electronic devices, for example, mobile phones and personal computers, has led to high-density integration of printed circuit boards as essential elements of the electronic devices. Such high-density integration is mainly achieved by layering printed circuit boards, reducing the thickness of printed circuit boards, making the diameter of through-holes smaller and reducing the interval of holes. Under these circumstances, there is a need for novel board materials that offer higher performance.

The use of high operating frequencies for rapid processing of large amounts of information in electronic information devices such as computers involves problems of transmission loss and signal delay. Generally, a signal delay in a printed circuit board increases linearly with the square root of the relative permittivity of an insulating material around interconnection lines. Thus, low-permittivity board materials are needed to produce printed circuit boards requiring a high transmission rate.

Liquid crystal polyester resins are board materials that have a dielectric constant as low as 3.0 and exhibit excellent characteristics, such as high heat resistance and low moisture absorption. The production of printed circuit boards using liquid crystal polyester resins is dependent on melting processes, such as injection molding, because most of the liquid crystal polymers are insoluble or slightly soluble in solvents. However, injection or extrusion of a liquid crystal polymer resin for the production of a printed circuit board renders the polymer highly anisotropic due to the orientation of the polymer chains, causing difficulty in designing a circuit. Further, the use of a liquid crystal polymer in a molten state for the production of a prepreg has the problem that impregnation of the liquid crystal polymer into a glass fiber doe not occur. In an attempt to solve this problem, a method was reported in which a solution of a liquid crystal polymer is cast to produce a film or prepreg. The solubilization of the liquid crystal polymer, however, requires a reduction in the number of constituent mesogen groups in the liquid crystal, which leads to a decrease in the glass transition temperature of the film or prepreg, which is indicative of poor heat resistance.

BRIEF SUMMARY OF THE INVENTION

Disclosed herein is a liquid crystal thermoset ("LCT") monomer or oligomer in which both ends are capped with maleimide having at least one methyl group, represented by Formula 1:

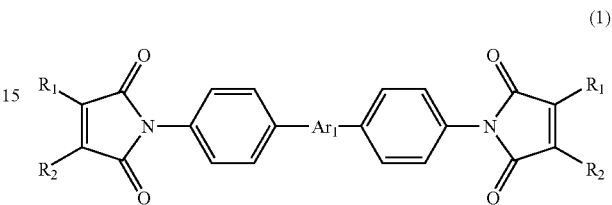

(1)

wherein $R_1$ and $R_2$ are each independently $CH_3$ or H, and at least one of $R_1$ and $R_2$ is a methyl group, and $Ar_1$ is a divalent organic group containing one or more structural units selected from the group consisting of ester, amide, ester amide, ester imide and ether imide units, and $Ar_1$ has a molecular weight not greater than 5,000.

In an exemplary embodiment, $Ar_1$ in Formula 1 may contain one or more structural units selected from the group consisting of, but not necessarily limited to, the following units 2:

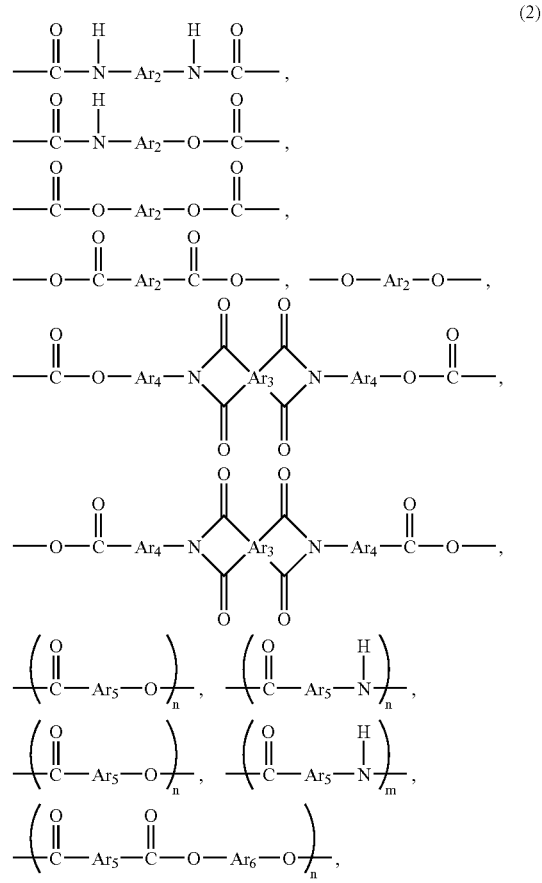

(2)

-continued

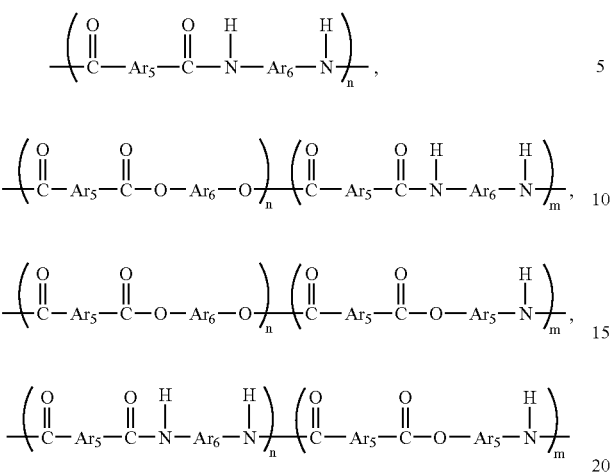

wherein $Ar_2$, $Ar_4$, $Ar_5$ and $Ar_6$ are each independently a divalent aromatic organic group containing one or more structural units selected from the group consisting of the following units 3:

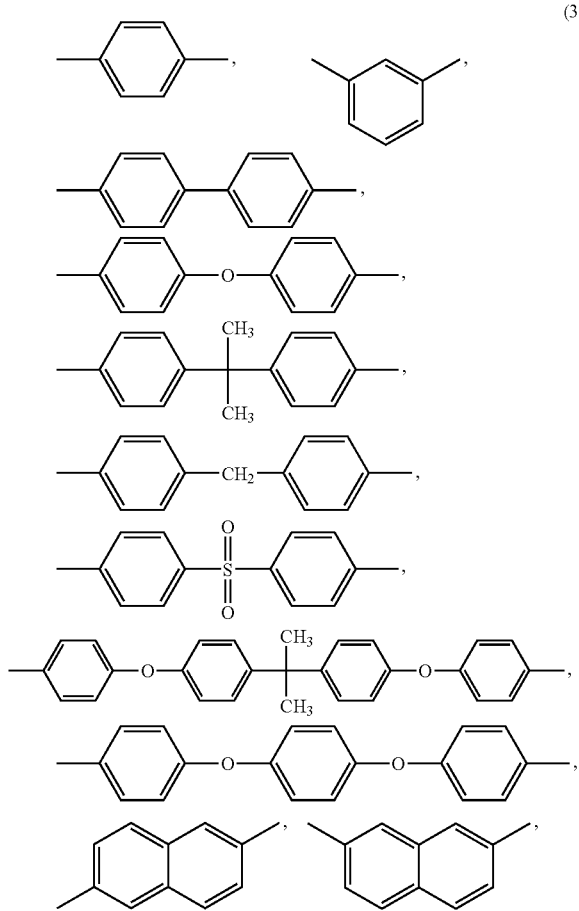

each $Ar_3$ is a tetravalent aromatic organic group containing one or more structural units selected from the group consisting of the following units 4:

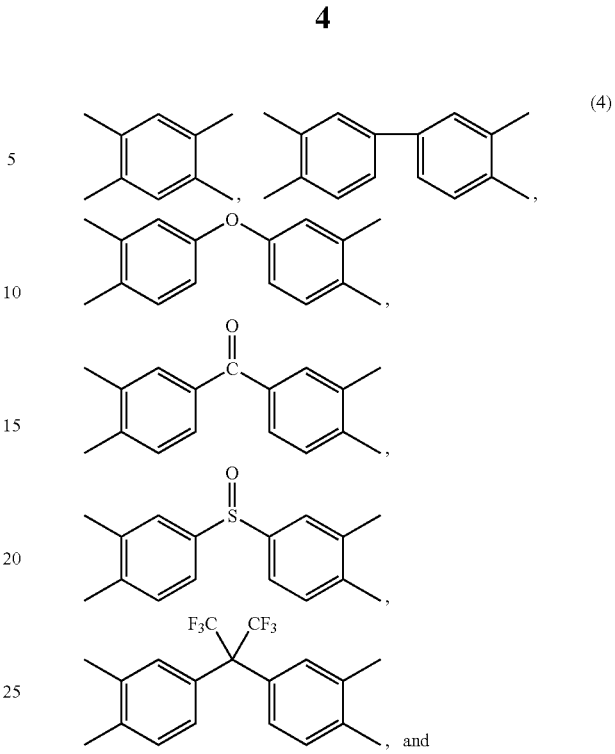

n and m are each independently an integer from 1 to 100.

The LCT monomer or oligomer exhibits excellent crosslinking properties and liquid crystallinity.

Disclosed herein too is a thermosetting liquid crystal polymer ("LCP") composition comprising the LCT monomer or oligomer and a liquid crystal polymer.

The LCP composition can be used to produce a printed circuit board with high heat resistance and excellent mechanical properties.

A printed circuit board using the LCT monomer or oligomer is also disclosed.

The printed circuit board has high heat resistance, excellent mechanical properties and improved handling properties.

BRIEF DESCRIPTION OF THE DRAWINGS

Exemplary embodiments will be more clearly understood from the following detailed description taken in conjunction with the accompanying drawings, in which.

DETAILED DESCRIPTION OF THE INVENTION

Figure 1:
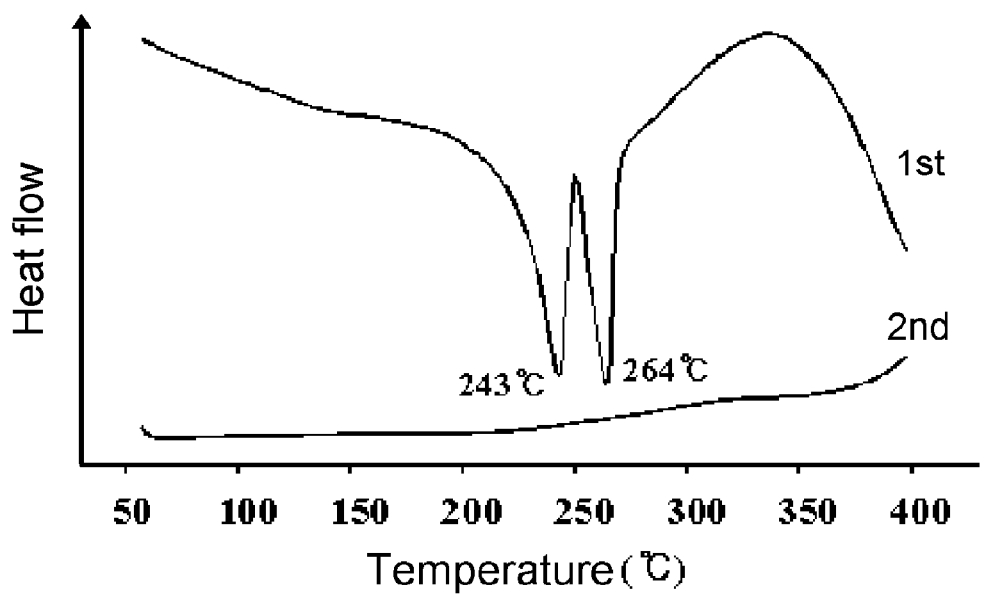
FIG. 1 is a graph showing the results of differential scanning calorimetry ("DSC") for a compound synthesized in Example 1.

Hereinafter, a detailed description will be given of exemplary embodiments with reference to the accompanying drawings.

It will be understood that when an element or layer is referred to as being "on," "interposed," "disposed," or "between" another element or layer, it can be directly on, interposed, disposed, or between the other element or layer or intervening elements or layers may be present.

It will be understood that, although the terms first, second, third, and the like may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

As used herein, the singular forms "a," "an" and "the" are intended to comprise the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

According to one embodiment, there is provided a liquid crystal thermoset ("LCT") monomer or oligomer having both ends capped with maleimide having at least one methyl group, represented by Formula 1:

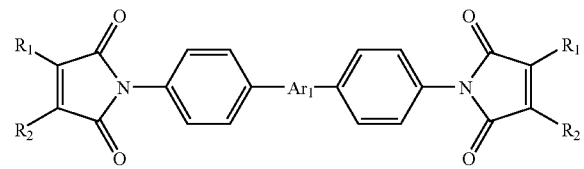

(1)

wherein $R_1$ and $R_2$ are each independently $CH_3$ or H, with the proviso that at least one of $R_1$ and $R_2$ is a methyl group, and $Ar_1$ is a divalent organic group containing one or more structural units selected from the group consisting of ester, amide, ester amide, ester imide and ether imide units, and having a molecular weight not greater than 5,000.

In an exemplary embodiment, $Ar_1$ in Formula 1 may contain one or more structural units selected from the group consisting of, but not necessarily limited to, the following units 2:

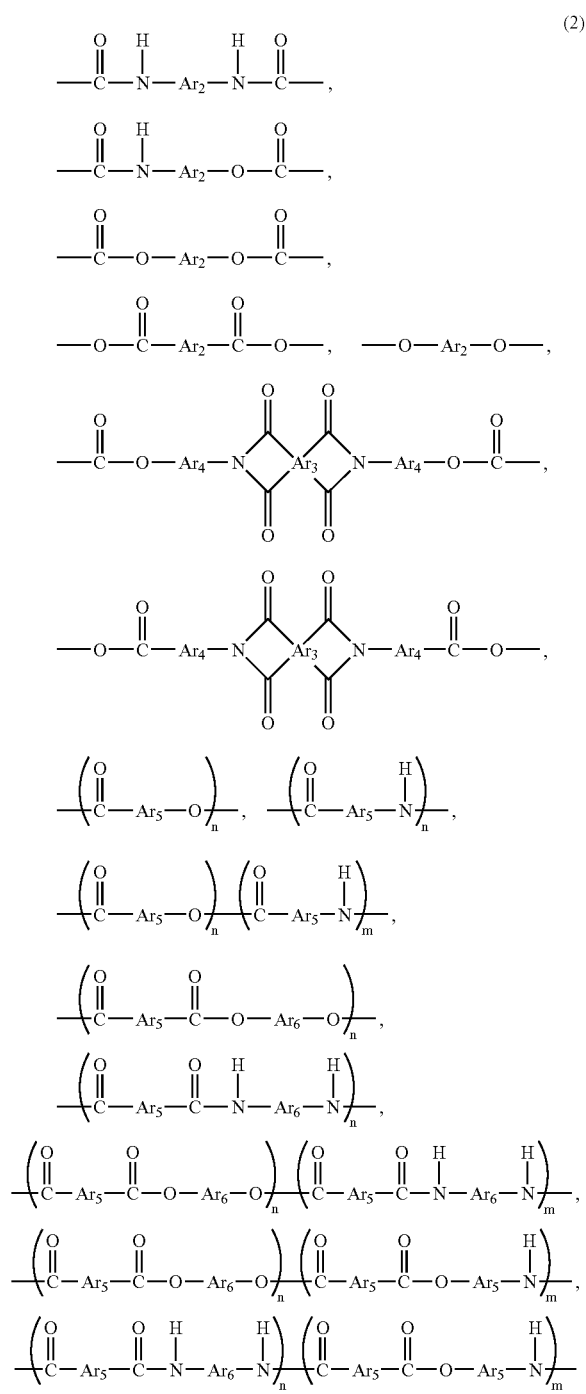

(2)

wherein $Ar_2$, $Ar_4$, $Ar_5$ and $Ar_6$ are each independently a divalent aromatic organic group containing one or more structural units selected from the group consisting of the following units 3:

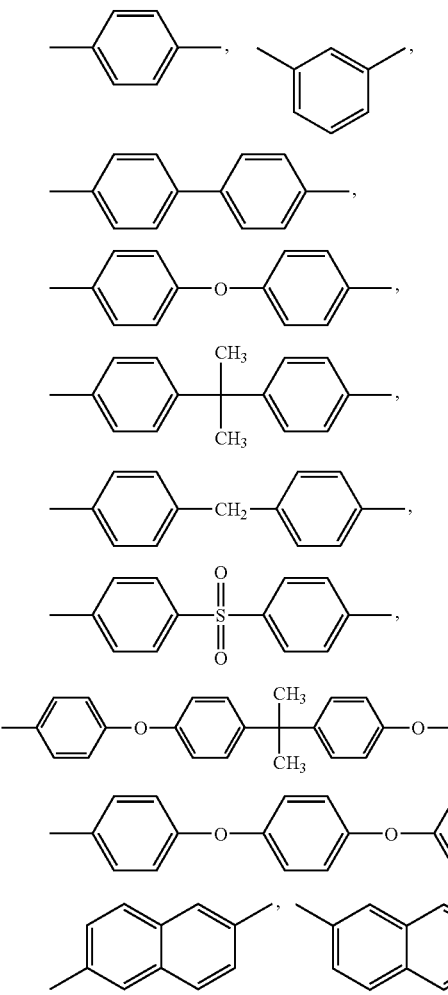
(3)
each Ar₃ is a tetravalent aromatic organic group containing one or more structural units selected from the group consisting of the following units 4:
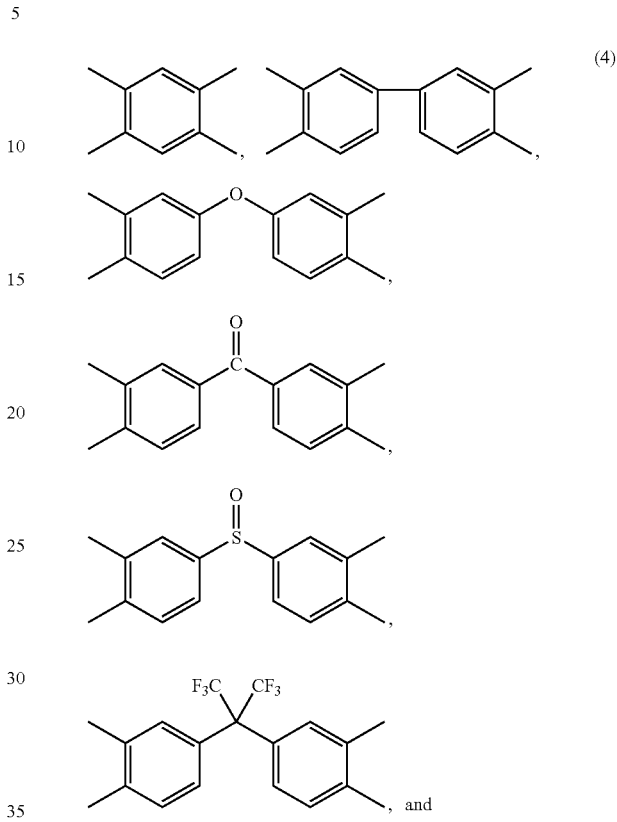
(4)
, and
n and m are each independently an integer from 1 to 100.
The LCT monomer or oligomer may be selected from, but not necessarily limited to, the following compounds of Formulae 5 to 20:
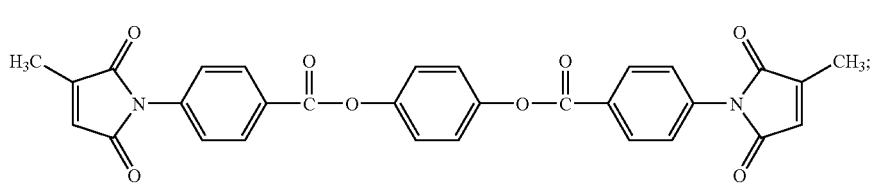
(5)
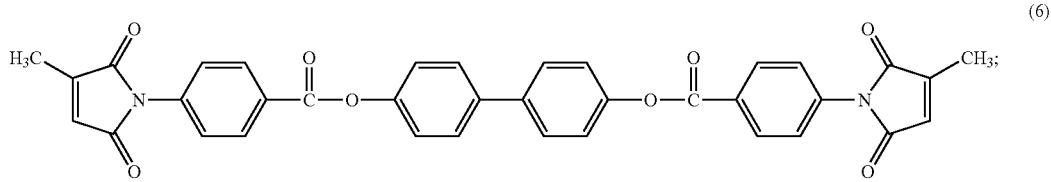
(6)
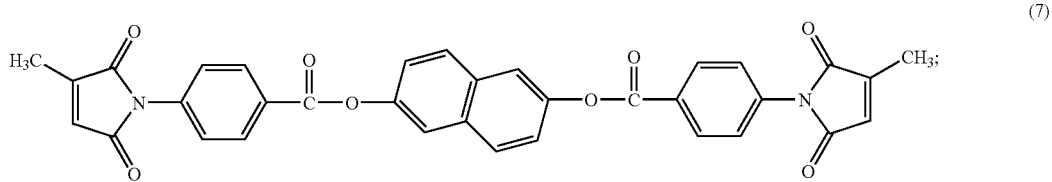
(7)

-continued
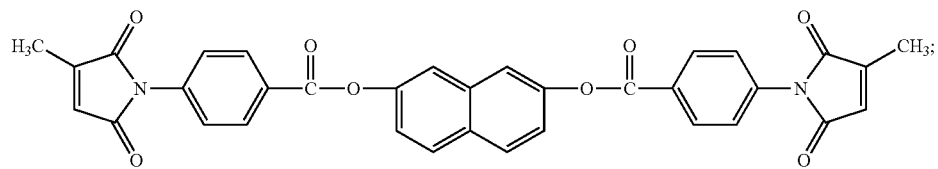
(8)
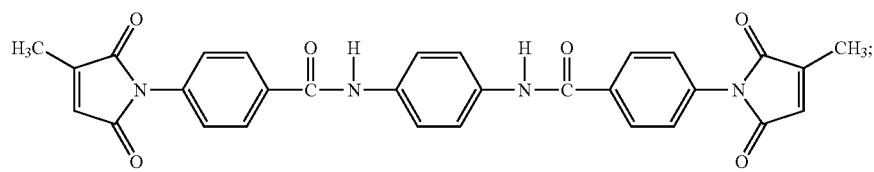
(9)
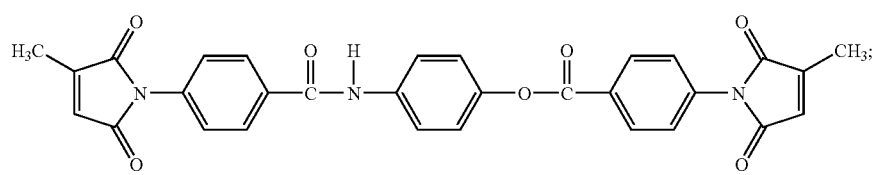
(10)
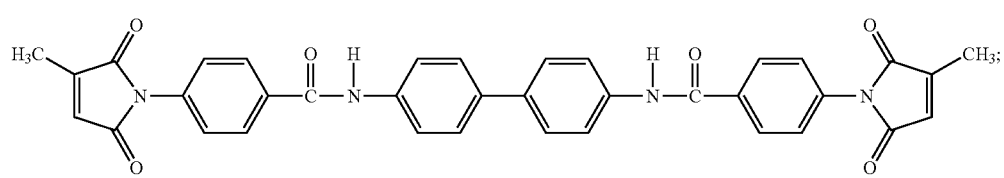
(11)
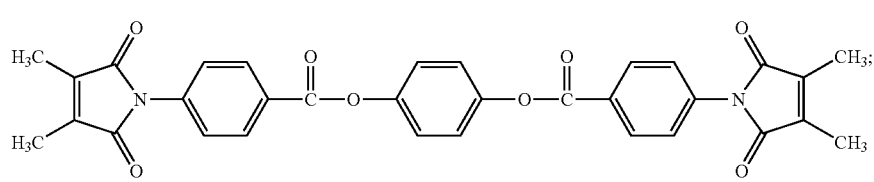
(12)
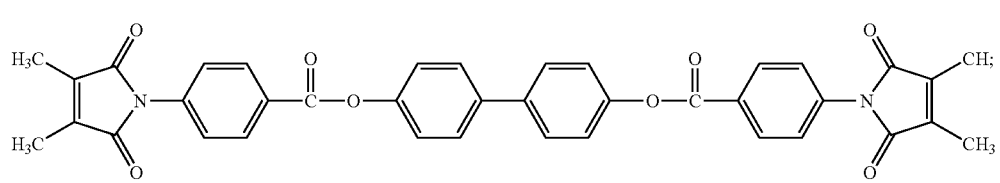
(13)
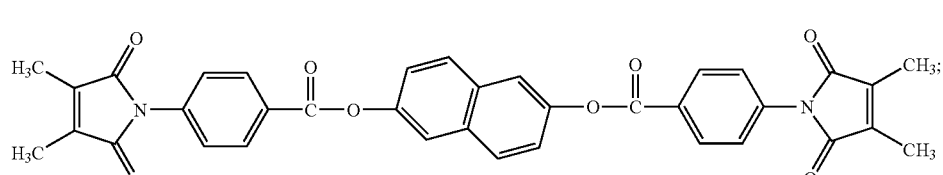
(14)
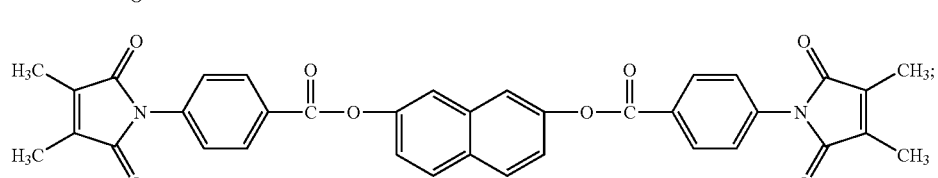
(15)
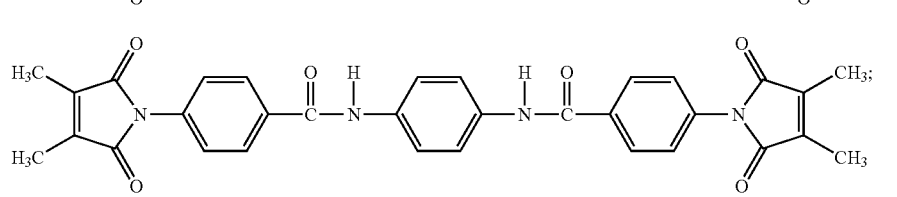
(16)

-continued

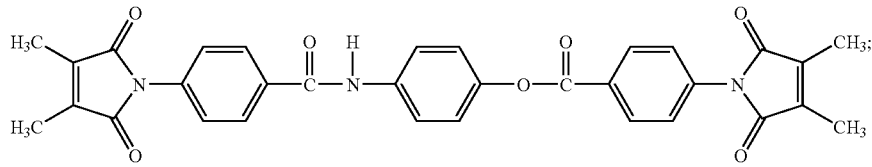

(17)

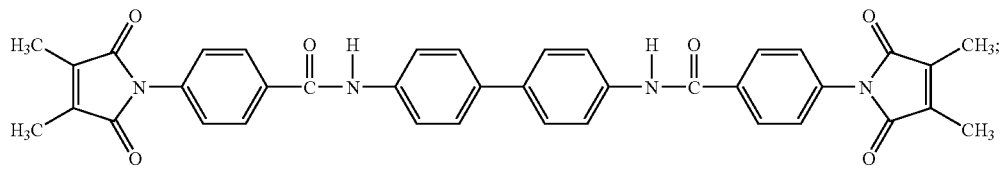

(18)

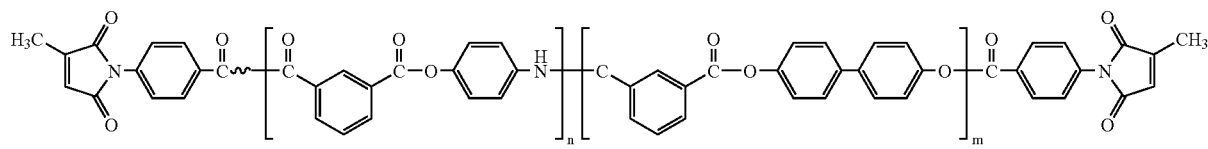

(19)

wherein m and n are each independently an integer from 1 to 30; and

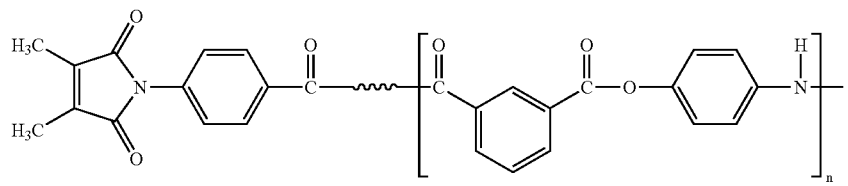

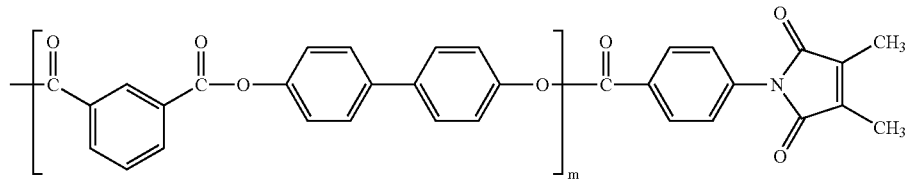

(20)

wherein m and n are each independently an integer from 1 to 30.

The molecular weight of the liquid crystal thermoset monomer or oligomer may be within the range of 300 to 5,000. The liquid crystal thermoset monomer or oligomer having a molecular weight lower than 300 is liable to be brittle due to its increased crosslinking density. Meanwhile, a solution containing the liquid crystal thermoset monomer or oligomer having a molecular weight higher than 5,000 may suffer from the disadvantage in that it is difficult to impregnate into a glass fiber due to its high viscosity.

In an exemplary embodiment, the mesogen of the liquid crystal thermoset monomer or oligomer is an amide ester structure. Suitable monomers for the mesogen include aromatic dicarboxylic acids, aromatic diamines, dihydroxybenzene, hydroxybenzoic acid, and aminobenzoic acid. The amide functional group serves to increase the solubility of the liquid crystal thermoset monomer or oligomer in a solvent. The aromatic structure, particularly a biphenyl or naphthalene structure, is used in forming a liquid crystal phase in exemplary embodiments.

There is no particular restriction on the method of preparing the liquid crystal thermoset monomer or oligomer. For example, solution or bulk polymerization can be carried out in one reaction tank equipped with suitable stirring means to prepare the liquid crystal thermoset monomer or oligomer. Specifically, the liquid crystal thermoset monomer or oligomer can be prepared from at least one aromatic, heterocyclic or aliphatic dicarboxylic acid, an aromatic, heterocyclic or aliphatic diol, a heterocyclic or aliphatic diamine, hydroxybenzoic acid, and aminobenzoic acid through a series of reactions depicted in Reaction Scheme 1:

1)

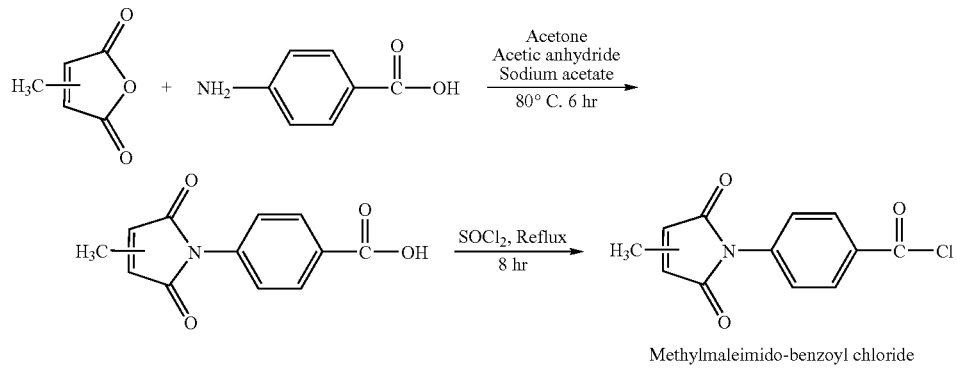

Methylmaleimido-benzoyl chloride

2)

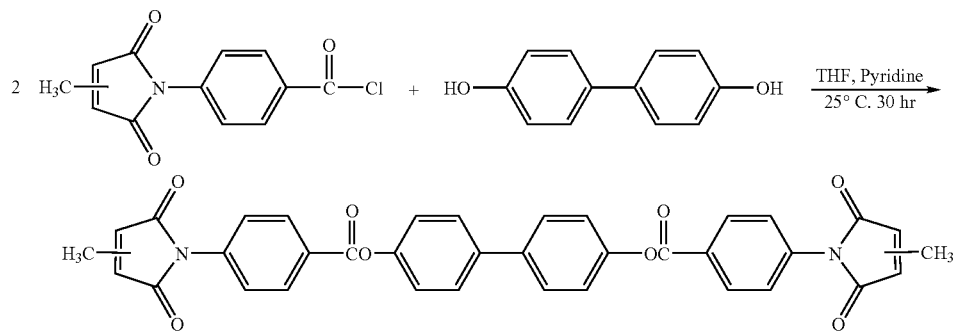

In accordance with another exemplary embodiment, a thermosetting liquid crystal polymer ("LCP") composition is provided, which comprises a liquid crystal thermoset ("LCT") monomer or oligomer and a liquid crystal polymer ("LCP").

The LCT monomer or oligomer ("LCT") monomer or oligomer has a structure represented by Formula 1:

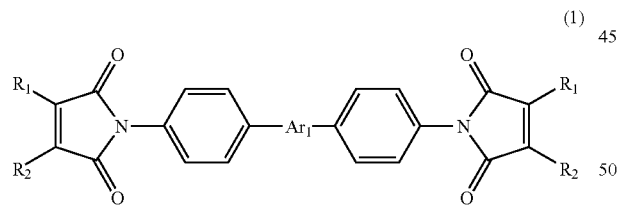

(1)

wherein $R_1$ and $R_2$ are each independently $CH_3$ or H, with the proviso that at least one of $R_1$ and $R_2$ is a methyl group, and $Ar_1$ is a divalent organic group containing one or more structural units selected from the group consisting of ester, amide, ester amide, ester imide and ether imide units, and having a molecular weight not greater than 5,000.

The LCT monomer or oligomer is characterized in that both ends of the monomer or oligomer are capped with maleimide having at least one methyl group.

In an exemplary embodiment, $Ar_1$ in Formula 1 may contain one or more structural units selected from the group consisting of, but not necessarily limited to, the following units 2:

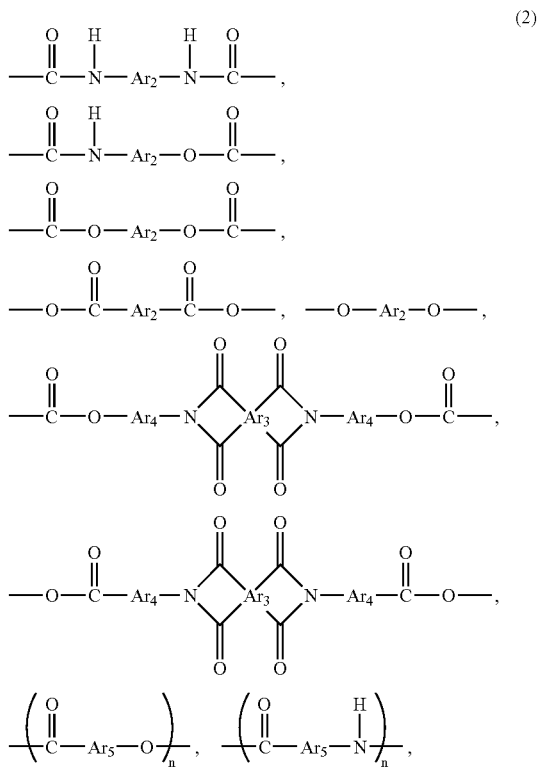

(2)

-continued

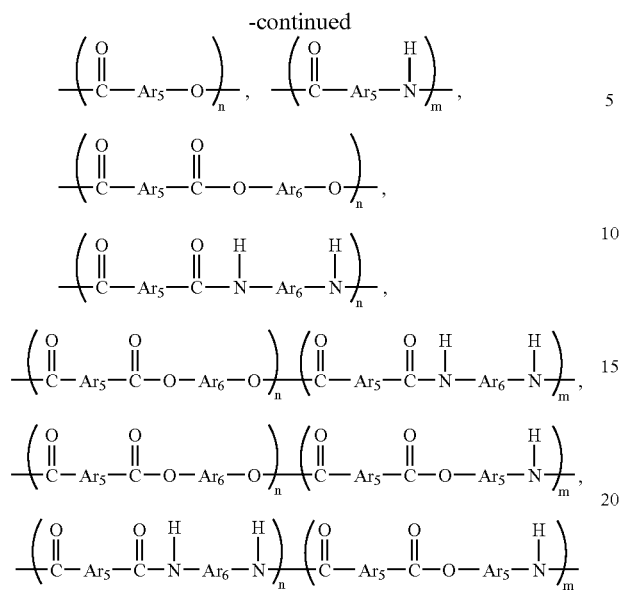

wherein $Ar_2$, $Ar_4$, $Ar_5$ and $Ar_6$ are each independently a divalent aromatic organic group containing one or more structural units selected from the group consisting of the following units 3:

(3)

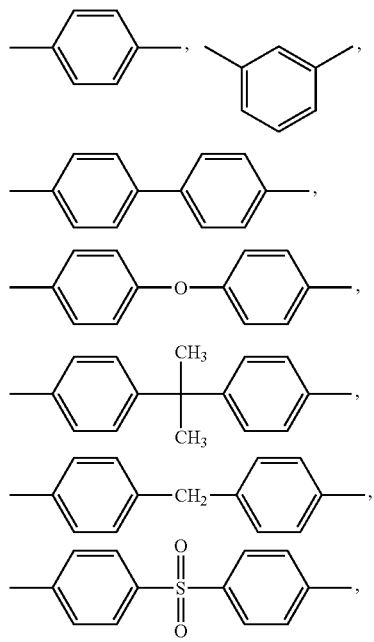

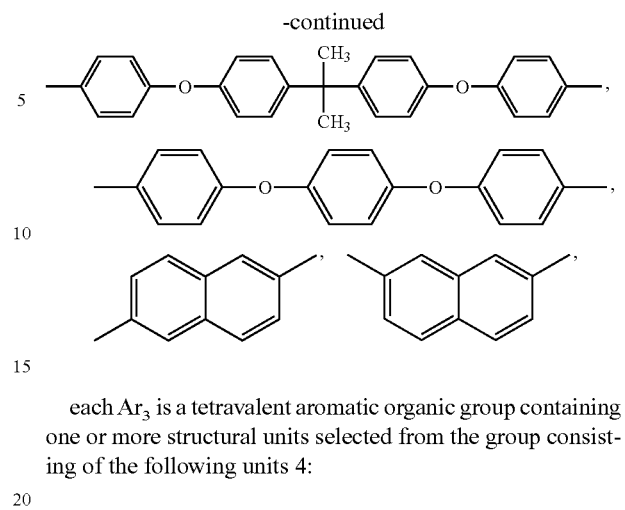

each $Ar_3$ is a tetravalent aromatic organic group containing one or more structural units selected from the group consisting of the following units 4:

(4)

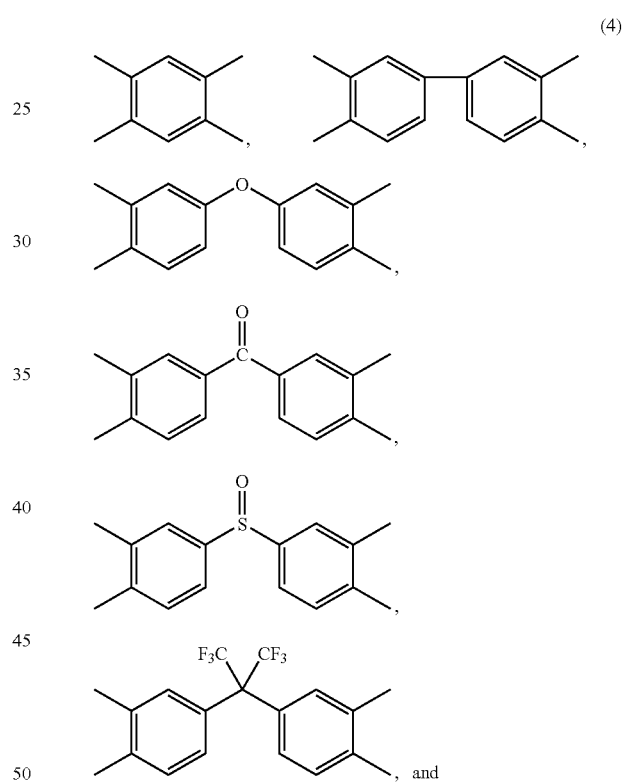

, and n and m are each independently an integer from 1 to 100.

The LCT monomer or oligomer may be selected from, but not necessarily limited to, the following compounds of Formulae 5 to 20:

(5)

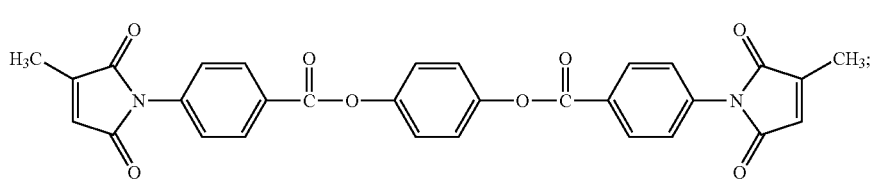

-continued
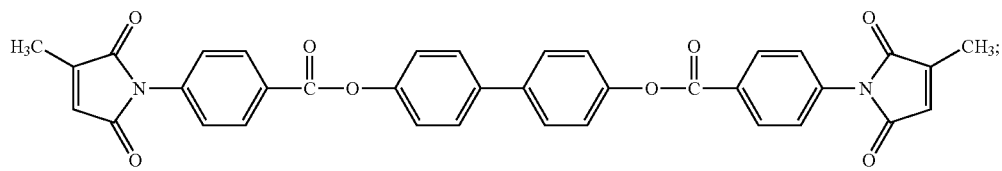
(6)
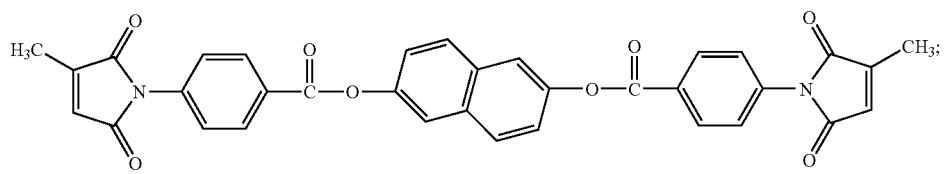
(7)
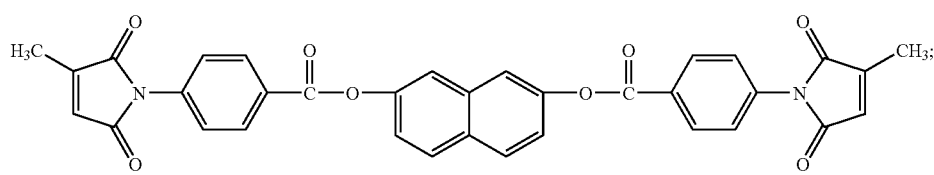
(8)
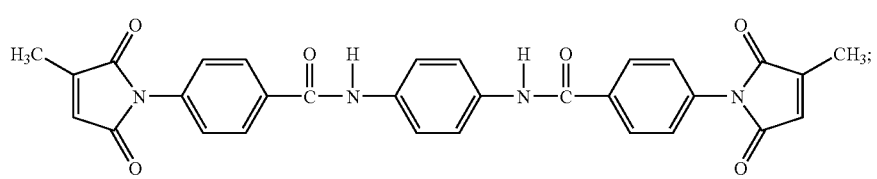
(9)
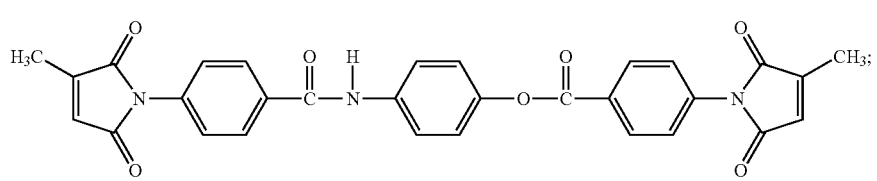
(10)
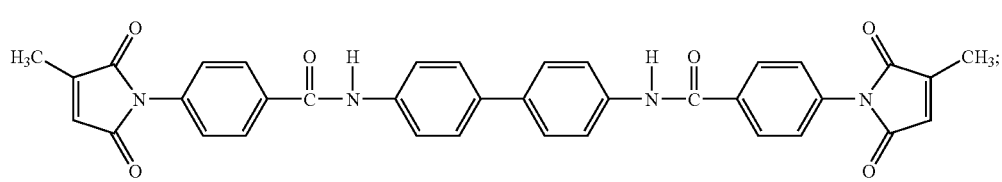
(11)
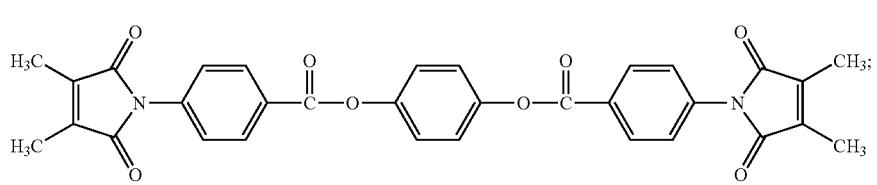
(12)
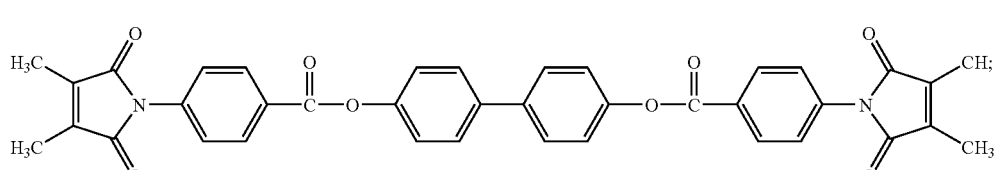
(13)
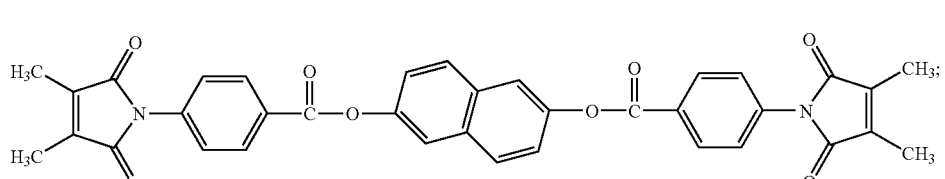
(14)

-continued

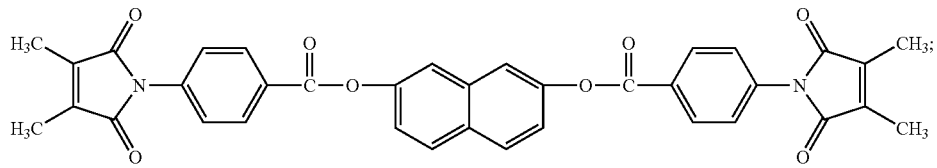
(15)

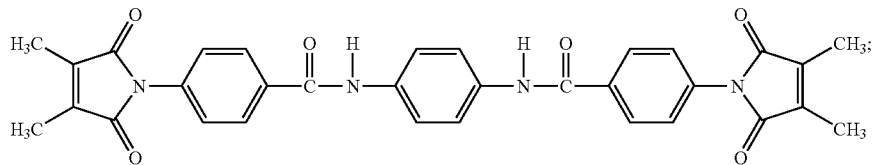
(16)

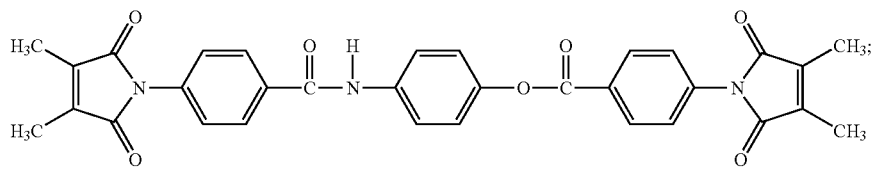
(17)

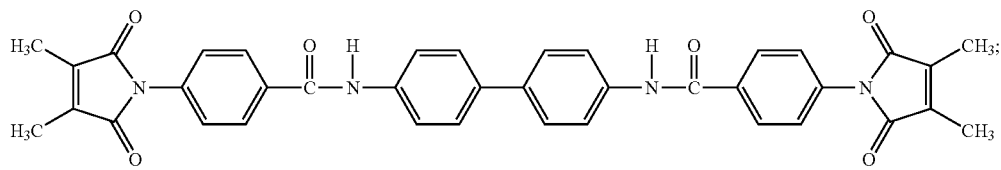
(18)

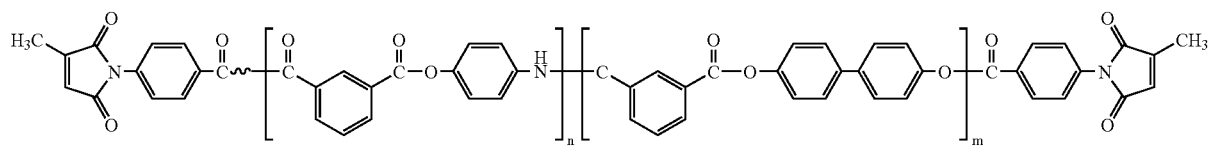
(19)

wherein m and n are each independently an integer from 1 to 30; and

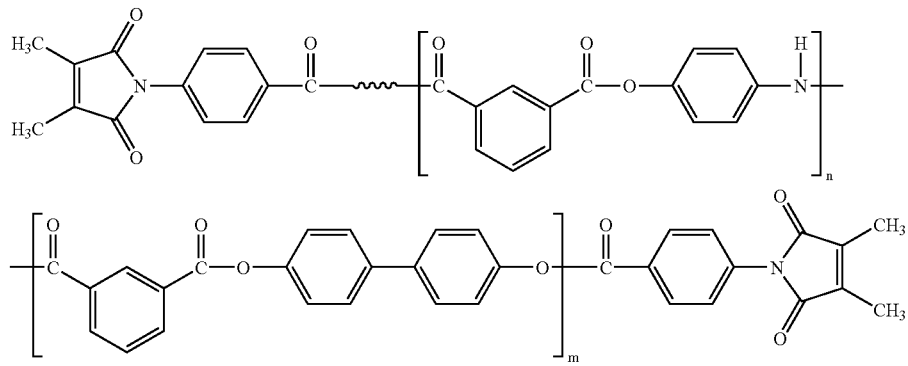
(20)

wherein m and n are each independently an integer from 1 to 30.

A printed circuit board is generally produced by impregnating a glass fiber with a thermosetting resin, e.g., an epoxy resin, to produce a prepreg and laminating a copper foil on the prepreg. In the case where a typical soluble liquid crystal polymer resin is used to produce a prepreg, the liquid crystal polymer must be dissolved in a suitable solvent to prepare a high-concentration varnish, which is then impregnated into a glass fiber. However, the high molecular weight of the liquid crystal polymer makes it difficult to increase the solids content of the varnish at an optimum viscosity. As a result, there is a limitation in increasing the amount of the resin impregnated into a glass fiber.

A prepreg produced using the thermosetting LCP composition, which comprises the liquid crystal thermoset monomer or oligomer in which both ends of the monomer or oligomer are capped with maleimide having at least one methyl group, has several advantages over a prepreg produced using a conventional liquid crystal polymer. Specifically, a varnish having a high solids content can be prepared to allow the liquid crystal thermoset monomer or oligomer to be readily impregnated into a glass fiber. In addition, the prepreg produced using the thermosetting LCP composition is thermally stable and has a low coefficient of thermal expansion after curing. Furthermore, the problem that the liquid crystal thermoset monomer or oligomer having terminal reactive groups is difficult to handle due to its brittleness before curing, can be overcome by the combined use of the high molecular weight liquid crystal polymer and the liquid crystal thermoset monomer or oligomer in the thermosetting LCP composition.

The liquid crystal polymer of the thermosetting LCP composition contains at least one structural unit selected from the following units 1, 2, 3 and 4:

(1)

wherein $Ar_1$ is 1,4-phenylene, 2,6-naphthylene or 4,4-biphenylene;

(2)

wherein $Ar_2$ is 1,4-phenylene, 1,3-phenylene or 2,6-naphthylene;

(3)

wherein X is NH, $Ar_3$ is 1,4-phenylene or 1,3-phenylene, and Y is O or NH; and

(4)

wherein $Ar_4$ is 1,4-phenylene or 1,3-phenylene.

It is to be understood that the liquid crystal polymer can contain structural units other than the units 1, 2, 3 and 4.

The structural units 1, 2, 3 and 4 are constituents of the liquid crystal polymer. The structural unit 1 is one derived from an aromatic hydroxycarboxylic acid, the structural unit 2 is one derived from an aromatic dicarboxylic acid, the structural unit 3 is one derived from an aromatic diamine or hydroxyamine, and the structural unit 4 is one derived from an aromatic aminocarboxylic acid.

Examples of suitable aromatic hydroxycarboxylic acids include p-hydroxybenzoic acid, 2-hydroxy-6-naphthoic acid and 4-hydroxy-4'-biphenylcarboxylic acid. The liquid crystal polymer may contain two or more of the structural units derived from the aromatic hydroxycarboxylic acids.

Examples of suitable aromatic dicarboxylic acids include terephthalic acid, isophthalic acid, 2,6-naphthalenedicarboxylic acid and diphenyl ether-4,4'-dicarboxylic acid. The liquid crystal polymer may contain two or more of the structural units derived from the aromatic dicarboxylic acids.

Examples of suitable aromatic diamines and hydroxyamines include 3-aminophenol, 4-aminophenol, 1,4-phenylenediamine and 1,3-phenylenediamine. The liquid crystal polymer may contain two or more of the structural units derived from the aromatic diamines and hydroxyamines.

Examples of suitable aromatic aminocarboxylic acids include 3-aminobenzoic acid, 4-aminobenzoic acid and 6-amino-2-naphthoic acid. The liquid crystal polymer may contain two or more of the structural units derived from the aromatic aminocarboxylic acids.

There is no particular restriction on the method of preparing the liquid crystal polymer. For example, the liquid crystal polymer can be prepared by acylating a phenolic hydroxyl group of an aromatic hydroxycarboxylic acid, from which the structural unit 1 is derived, with an amino group of an aromatic hydroxylamine or diamine, from which the structural unit 2 is derived, in an excess of a fatty acid anhydride to obtain a corresponding acyl compound, and melt-polycondensing (e.g., transesterifying) the acyl compound with an aromatic dicarboxylic acid, from which the structural unit 3 is derived.

The molecular weight of the liquid crystal polymer is in the range of 5,000 to 500,000 in exemplary embodiments, but is not particularly limited to this range.

The thermosetting LCP composition may comprise 5 to 80 parts by weight of the liquid crystal polymer and 20 to 95 parts by weight of the liquid crystal thermoset monomer or oligomer.

The thermosetting LCP composition may further comprise an aprotic solvent suitable for solvent casting to prevent a deterioration in mechanical properties due to the anisotropicity of the liquid crystal. The liquid crystal thermoset monomer or oligomer may be soluble in the aprotic solvent.

There is no particular restriction on the kind of aprotic solvents usable herein. The aprotic solvent can be selected from N,N-dimethylacetamide, N-methylpyrrolidone, N-methylcaprolactam, N,N-dimethylformamide, N,N-diethylformamide, N,N-diethylacetamide, N-methylpropionamide, dimethylsulfoxide, y-butyrolactone, dimethylimidazolidinone, tetramethylphosphoramide, and ethyl cellosolve acetate. These solvents may be used alone or as a mixture of two or more thereof.

The solids content of the composition is preferably not lower than 25 parts by weight, based on 100 parts by weight of the solvent. When the solids content is lower than 25 parts by weight, the amounts of the liquid crystal thermoset monomer or oligomer and the liquid crystal polymer impregnated into a glass fiber are disadvantageously small.

If necessary, the thermosetting LCP composition may further comprise one or more additives selected from fillers, softeners, plasticizers, lubricants, antistatic agents, colorants, antioxidants, heat stabilizers, light stabilizers and UV absorbers, so long as the aspects, feature and advantages of the present invention can be accomplished. Examples of suitable fillers include organic fillers, such as epoxy, melamine, urea, benzoguanamine and styrene resin powders, and inorganic fillers, such as silica, alumina, titanium oxide, zirconia, kaolin, calcium carbonate and calcium phosphate.

The thermosetting LCP composition exhibits liquid crystallinity and has high crosslinking density. In addition, the thermosetting LCP composition can be more advantageously impregnated into a glass fiber because of its lower viscosity than the liquid crystal polymer. Based on these advantages, the composition can be used to produce films, sheets and composite materials with low coefficient of thermal expansion and low dielectric constant. The use of such articles allows for the production of high-performance printed circuit boards.

The thermosetting LCP composition can be used as a next-generation packaging material due to its good adhesion to a copper foil, high heat resistance, low thermal expansion and excellent mechanical properties. The thermosetting LCP composition can be molded into a board or prepared into a varnish for impregnation or coating applications. Other applications of the composition include laminates, printed boards, layers of multilayer boards, resin-coated copper foils, copper clad laminates, polyimide films, TAB films and prepregs, but are not limited thereto.

For example, a board material can be produced by casting the composition, which comprises the liquid crystal polymer and the liquid crystal thermoset monomer or oligomer, on a substrate to form a thin film and curing the thin film at high temperature. The addition of the liquid crystal polymer having a high molecular weight improves the flexibility of the board and facilitates handling during subsequent lamination of a copper foil on the board.

A prepreg can be produced by impregnating a glass fiber with the thermosetting LCP composition and removing the aprotic solvent. The impregnation can be carried out by any technique known in the art, such as dip coating or roll coating, for example, but is not limited thereto.

A copper clad laminate can be produced by applying the thermosetting LCP composition to a copper foil or casting the composition on a copper foil, removing the solvent, followed by annealing. The solvent is removed by evaporation in exemplary embodiments. The evaporation is carried out under reduced pressure or by ventilation.

Examples of suitable techniques for applying the thermosetting LCP composition include, but are not necessarily limited to, roll coating, dip coating, spray coating, spin coating, curtain coating, slot coating and screen printing. Fine impurities contained in the thermosetting LCP composition are removed by filtration before application to or casting on a copper foil in exemplary embodiments.

Instead of the copper foil, other metal foils (e.g., aluminum foils) may be used. The thickness of the metal foil may vary depending on the desired application. The metal foil has a thickness of 5 to 100 μm in exemplary embodiments. A printed circuit board can be produced by performing circuit processing on a metal foil of a metal foil-coated laminate. A multilayer printed circuit board can be produced by stacking another metal foil-coated laminate on the printed laminate and performing circuit processing on the stack.

A better understanding of exemplary embodiments will be described in more detail with reference to the following Examples. However, these Examples are given merely for the purpose of illustration and are not to be construed as limiting the scope of the exemplary embodiments.

EXAMPLES

Preparative Example 1

Synthesis of Methylmaleimido-benzoyl Chloride 33.6 g (0.3 mol) of citraconic anhydride was slowly added to a solution of 41.1 g (0.3 mol) of p-aminobenzoic acid and 300 ml of acetone in a 250 ml flask at 10° C. The mixture was stirred for 2 hours to obtain a yellow precipitate. Thereafter, the precipitate was collected by filtration under reduced pressure and recrystallized from a solution of dimethylformamide ("DMF")/ethanol (50:50 (w/w)) to give an intermediate as a yellow powder. The intermediate was treated with sodium acetate and acetic anhydride at 85° C. for 4 hours, cooled to room temperature, and placed in an ice bath to obtain a precipitate. The precipitate was collected by filtration under reduced pressure and recrystallized from a solution of ethanol/water (50:50 (w/w)) to give N-(p-carboxyphenyl)methylmaleimide.

16.2 g (0.07 mol) of the N-(p-carboxyphenyl)methylmaleimide was dissolved in 60 ml of thionyl chloride, and 1 ml of pyridine was slowly added thereto. The mixture was refluxed at 80° C. for 3 hours. After the reaction was finished, unreacted thionyl chloride was removed using an evaporator. The reaction mixture was cooled to room temperature, filtered, and washed with hexane to afford 11 g (yield 68%) of methylmaleimido-benzoyl chloride.

Preparative Example 2

Synthesis of Dimethylmaleimido-benzoyl Chloride 37.8 g (0.3 mol) of dimethylmaleic anhydride was slowly added to a solution of 41.1 g (0.3 mol) of p-aminobenzoic acid and 300 ml of acetone in a 250 ml flask at 10° C. The mixture was stirred for 2 hours to obtain a yellow precipitate. Thereafter, the precipitate was collected by filtration under reduced pressure and recrystallized from a solution of DMF/water (50:50 (w/w)) to give an intermediate. The intermediate was treated with sodium acetate and acetic anhydride at 85° C. for 4 hours, cooled to room temperature, and placed in an ice bath to obtain a precipitate. The precipitate was collected by filtration under reduced pressure and recrystallized from a solution of ethanol/water (50:50 (w/w)) to give N-(p-carboxyphenyl)dimethylmaleimide.

17.2 g (0.07 mol) of the N-(p-carboxyphenyl)dimethylmaleimide was dissolved in 60 ml of thionyl chloride, and 1 ml of pyridine was slowly added thereto. The mixture was refluxed at 80° C. for 3 hours. After the reaction was finished, unreacted thionyl chloride was removed using an evaporator. The reaction mixture was cooled to room temperature, filtered, and washed with hexane to afford 12.5 g (yield 73%) of dimethylmaleimido-benzoyl chloride.

Example 1

Synthesis of Liquid Crystal Thermoset ("LCT") Monomer

The methylmaleimido-benzoyl chloride (10 g, 0.04 mol) synthesized in Preparative Example 1 was dissolved in tetrahydrofuran ("THF") in a 250 ml flask, and then a solution of 2.2 g (0.02 mol) of hydroquinone in pyridine was slowly added dropwise thereto. The mixture was allowed to react at room temperature for 16 hours. The reaction mixture was poured into water to obtain a precipitate. The precipitate was collected by filtration under reduced pressure and washed with ethanol, affording the bis(methylmaleimide) compound of Formula 5:

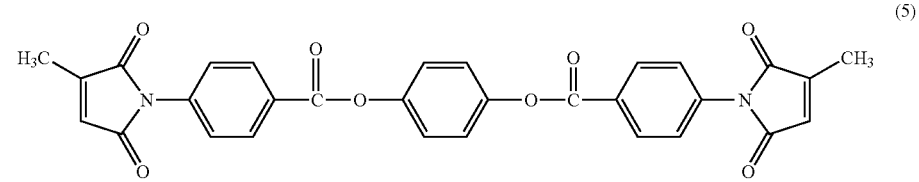

(5)

Figure 9:
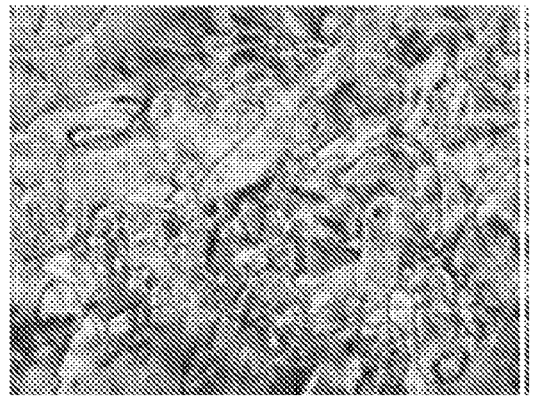
FIG. 9 is an optical micrograph showing the liquid crystal phase of a compound synthesized in Example 1.

The thermal properties of the product were evaluated using a differential scanning calorimeter ("DSC"), (DSC 2010, TA Instruments). The obtained DSC curves are shown in FIG. 1. Referring to FIG. 1, the melting point ($T_m$) and the isotropic point ($T_i$) of the product were determined from two endothermic peaks, which are found during the first heating run (i.e., "$1^{st}$") The curve for the second heating run (i.e., "$2^{nd}$") demonstrates the completion of crosslinking. The liquid crystallinity of the product was observed under a hot-stage optical microscope. Specifically, the observation was made as to whether a liquid crystal was formed while raising the temperature by one degree Celsius from the melting point determined in the DSC analysis. FIG. 9 is an optical micrograph (magnification: 250×) showing the liquid crystal phase of the product at 258° C. The micrograph reveals that the liquid crystal phase was nematic. The results of the DSC and liquid crystallinity analyses are summarized in Table 1 below.

Example 2

Synthesis of Liquid Crystal Thermoset ("LCT") Monomer

The bis(methylmaleimide) compound of Formula 6 was synthesized in the same manner as in Example 1 except that 3.7 g (0.02 mol) of 4,4'-biphenol was used instead of 2.2 g (0.02 mol) of hydroquinone.

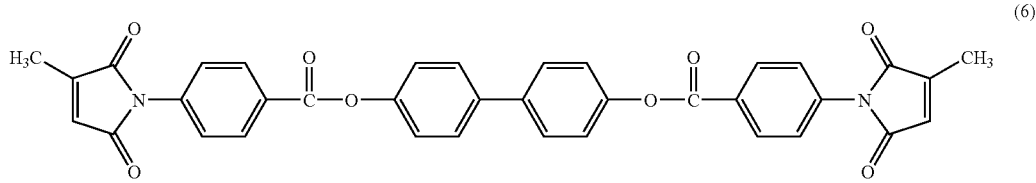

(6)

Figure 2:
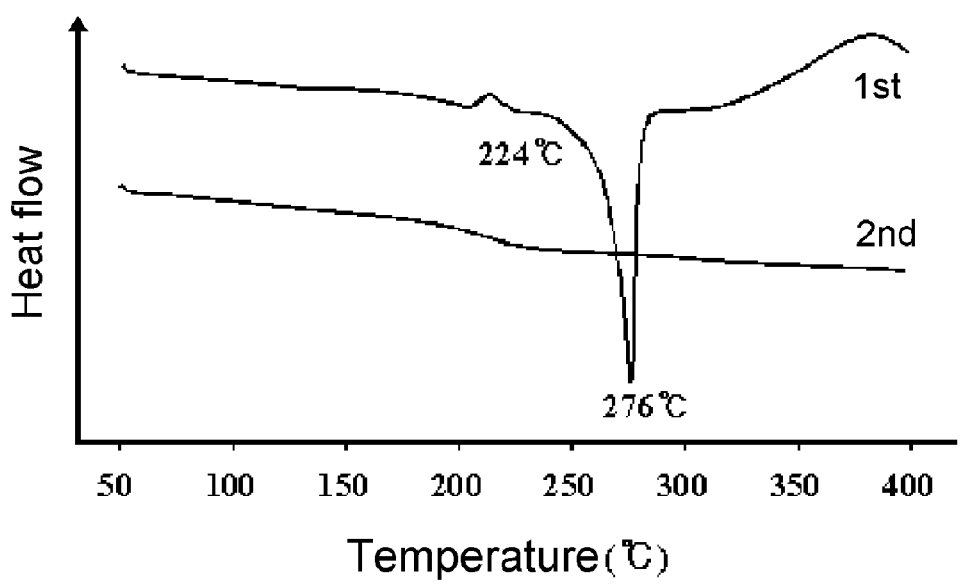
FIG. 2 is a graph showing the results of DSC for a compound synthesized in Example 2.
Figure 10:
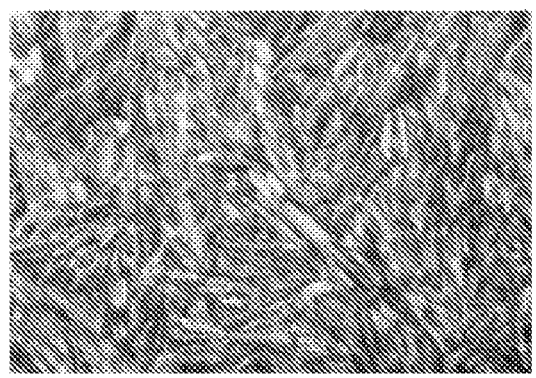
FIG. 10 is an optical micrograph showing the liquid crystal phase of a compound synthesized in Example 2.

The thermal properties and the liquid crystallinity of the product were evaluated by the methods described in Example 1. FIG. 2 shows DSC curves of the product, and FIG. 10 is an optical micrograph (magnification: 250×) showing the liquid crystal phase of the product at 260° C. The micrograph reveals that the liquid crystal phase was nematic. The results of the DSC and liquid crystallinity analyses are summarized in Table 1 below.

Example 3

Synthesis of Liquid Crystal Thermoset ("LCT") Monomer

The bis(methylmaleimide) compound of Formula 7 was synthesized in the same manner as in Example 1 except that 2.6 g (0.02 mol) of 2,6-dihydroxynaphthalene was used instead of 2.2 g (0.02 mol) of hydroquinone.

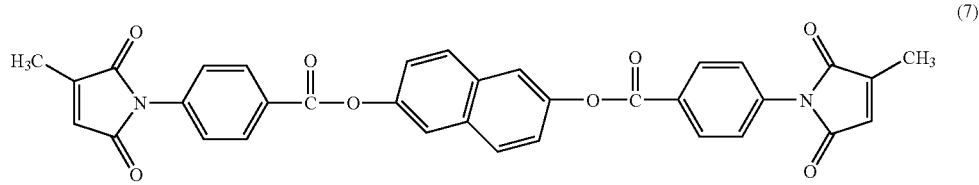

(7)

Figure 3:
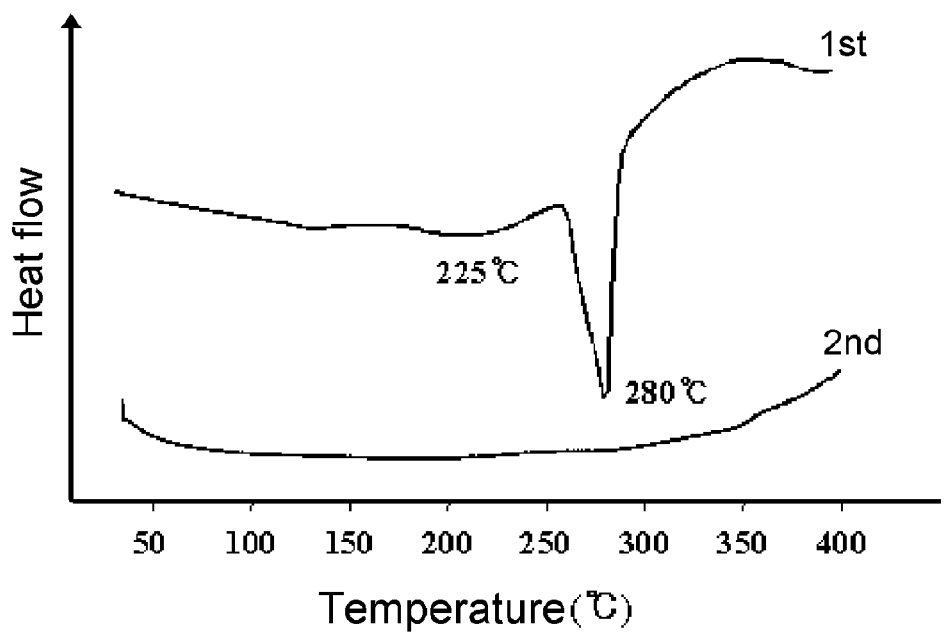
FIG. 3 is a graph showing the results of DSC for a compound synthesized in Example 3.
Figure 11:
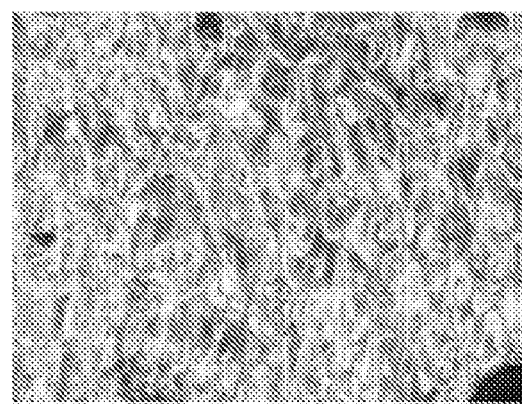
FIG. 11 is an optical micrograph showing the liquid crystal phase of a compound synthesized in Example 3.

The thermal properties and the liquid crystallinity of the product were evaluated by the methods described in Example 1. FIG. 3 shows DSC curves of the product, and FIG. 11 is an optical micrograph (magnification: 250×) showing the liquid crystal phase of the product at 258° C. The micrograph reveals that the liquid crystal phase was nematic. The results of the DSC and liquid crystallinity analyses are summarized in Table 1 below.

Example 4

Synthesis of Liquid Crystal Thermoset ("LCT") Monomer 2.2 g (0.02 mol) of 1,4-phenylenediamine and 4.5 g of triethylamine were dissolved in 30 ml of THF in a 250 ml flask, and then a solution of the methylmaleimido-benzoyl chloride (10 g, 0.04 mol) synthesized in Preparative Example 1 in 50 ml of THF was slowly added dropwise thereto. The mixture was allowed to react at room temperature for 16 hours. The reaction mixture was poured into water to obtain a precipitate. The precipitate was collected by filtration under reduced pressure and washed with ethanol, affording the bis (methylmaleimide) compound of Formula 9:

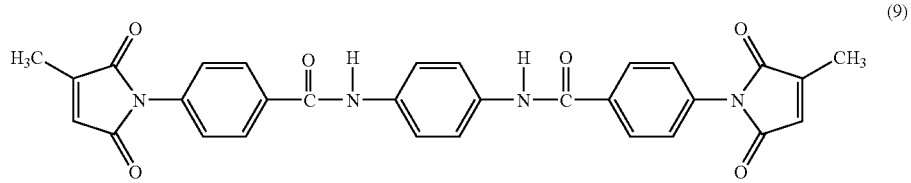

(9)

The results of DSC and liquid crystallinity analyses for the product are summarized in Table 1 below.

Example 5

Synthesis of Liquid Crystal Thermoset ("LCT") Monomer

The bis(methylmaleimide) compound of Formula 10 was synthesized in the same manner as in Example 4 except that 2.2 g (0.02 mol) of 4-aminophenol was used instead of 1,4-phenylenediamine.

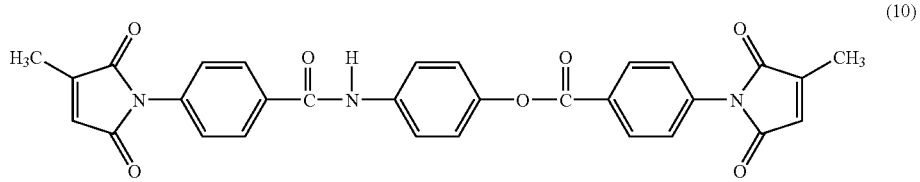

(10)

The results of DSC and liquid crystallinity analyses for the product are summarized in Table 1 below.

Example 6

Synthesis of Liquid Crystal Thermoset ("LCT") Monomer

The bis(methylmaleimide) compound of Formula 11 was synthesized in the same manner as in Example 4 except that 3.7 g (0.02 mol) of benzidine was used instead of 1,4-phenylenediamine.

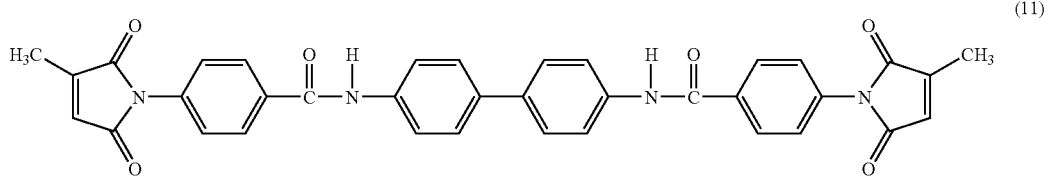

(11)

The results of DSC and liquid crystallinity analyses for the product are summarized in Table 1.

TABLE 1

|  | Melting point ($T_m$, °C.) | Isotropic point ($T_i$, °C.) | $\Delta H_m$ (J/g) | $\Delta H_i$ (J/g) | LC phase |
| --- | --- | --- | --- | --- | --- |
| Example 1 | 243 | 264 | 30.09 | 21.72 | Nematic |
| Example 2 | 227 | 276 | 1.46 | 74.92 | Nematic |
| Example 3 | 225 | 280 | 10.5 | 55.67 | Nematic |
| Example 4 | 250 | 278 | 20.01 | 32.21 | Nematic |
| Example 5 | 248 | 269 | 12.55 | 36.02 | Nematic |
| Example 6 | 261 | 283 | 32.01 | 55.26 | Nematic |

Note
$\Delta H_m$: The amount of heat generated upon melting
$\Delta H_i$: The amount of heat generated when each liquid crystal in a molten state was converted to an isotropic phase Example 7

Synthesis of Liquid Crystal Thermoset ("LCT") Monomer

The bis(dimethylmaleimide) compound of Formula 12 was synthesized in the same manner as in Example 1 except that 10 g (0.038 mol) of dimethylmaleimido-benzoyl chloride synthesized in Preparative Example 2 and 2.1 g (0.019 mol) of hydroquinone were used.

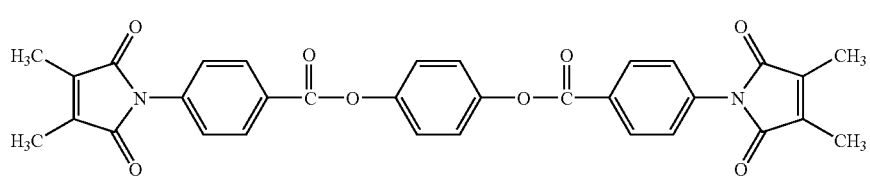

(12)

Figure 4:
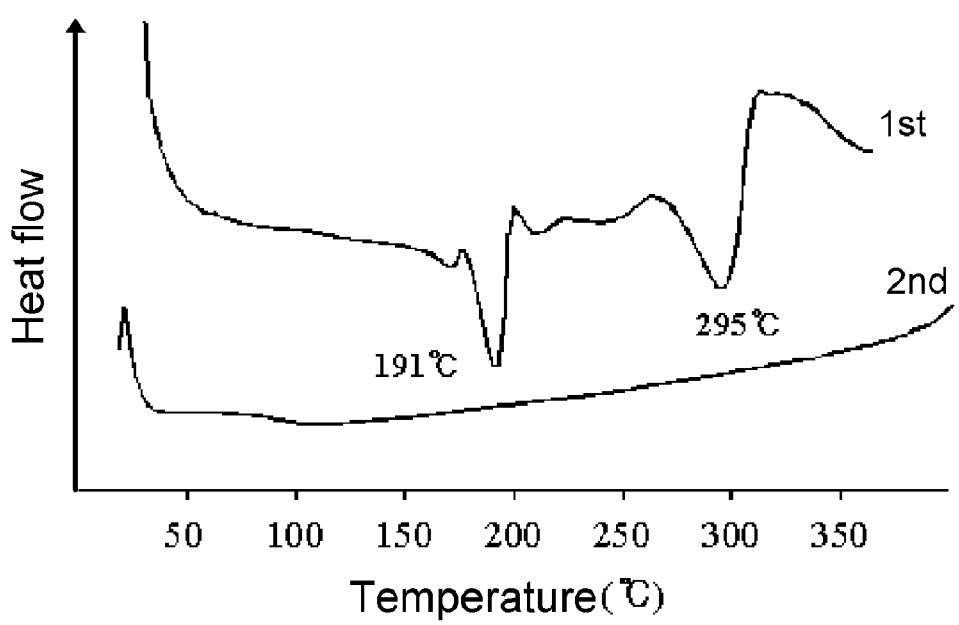
FIG. 4 is a graph showing the results of DSC for a compound synthesized in Example 7.
Figure 12:
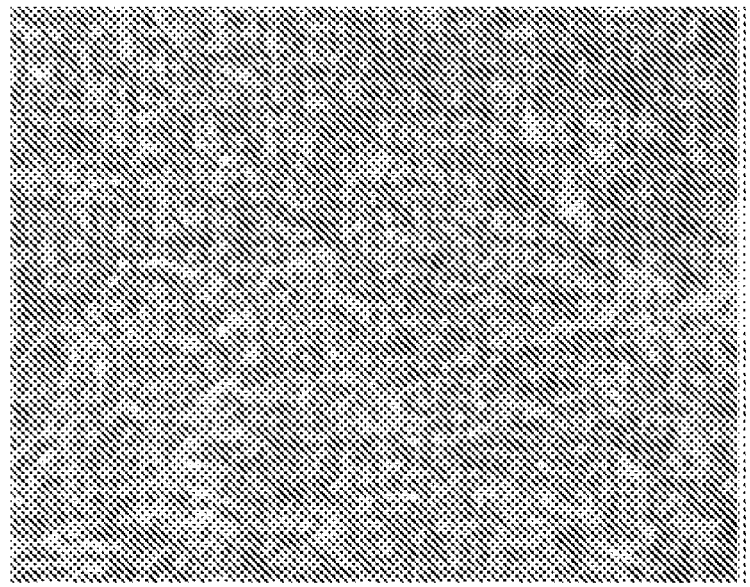
FIG. 12 is an optical micrograph showing the liquid crystal phase of a compound synthesized in Example 7.

The thermal properties and the liquid crystallinity of the product were evaluated by the methods described in Example 1. FIG. 4 shows DSC curves of the product, and FIG. 12 is an optical micrograph (magnification: 250×) showing the liquid crystal phase of the product at 250° C. The micrograph reveals that the liquid crystal phase was nematic. The results of the DSC and liquid crystallinity analyses are summarized in Table 2 below.

Example 8

Synthesis of Liquid Crystal Thermoset ("LCT") Monomer

The bis(dimethylmaleimide) compound of Formula 13 was synthesized in the same manner as in Example 7 except that 3.7 g (0.019 mol) of 4,4'-biphenol was used instead of 2.1 g (0.019 mol) of hydroquinone.

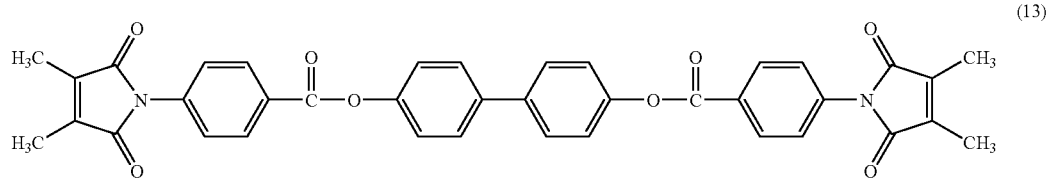

(13)

The thermal properties and the liquid crystallinity of the product were evaluated by the methods described in Example 1. The results of the DSC and liquid crystallinity analyses are summarized in Table 2 below.

Example 9

Synthesis of Liquid Crystal Thermoset ("LCT") Monomer 2.16 g (0.02 mol) of 1,4-phenylenediamine and 4.5 g of triethylamine were dissolved in 30 ml of THF in a 250 ml flask, and then a solution of the dimethylmaleimido-benzoyl chloride (10.55 g, 0.04 mol) synthesized in Preparative Example 2 in 50 ml of THF was slowly added dropwise thereto. The mixture was allowed to react at room temperature for 16 hours. The reaction mixture was poured into water to obtain a precipitate. The precipitate was collected by filtration under reduced pressure and washed sequentially with water and ethanol, affording the bis(dimethylmaleimide) compound of Formula 16.

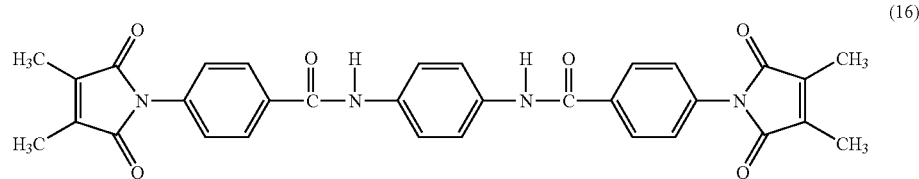

(16)

The results of DSC and liquid crystallinity analyses for the product are summarized in Table 2 below.

Example 10

Synthesis of Liquid Crystal Thermoset ("LCT") Monomer

The bis(dimethylmaleimide) compound of Formula 17 was synthesized in the same manner as in Example 9 except that 2.18 g (0.02 mol) of 4-aminophenol was used instead of 1,4-phenylenediamine.

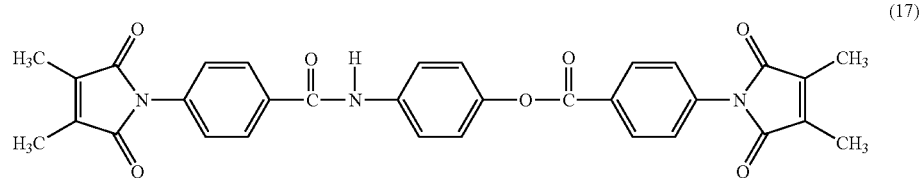

(17)

The results of DSC and liquid crystallinity analyses for the product are summarized in Table 2 below.

Example 11

Synthesis of Liquid Crystal Thermoset ("LCT") Monomer

The bis(dimethylmaleimide) compound of Formula 18 was synthesized in the same manner as in Example 9 except that 3.68 g (0.02 mol) of benzidine was used instead of 1,4-phenylenediamine.

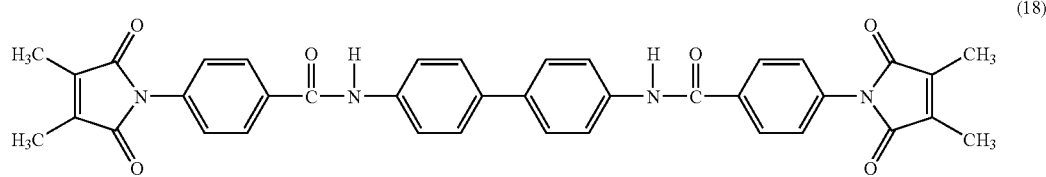

(18)

The results of DSC and liquid crystallinity analyses for the product are summarized in Table 2.

TABLE 2

|  | $T_m$ (° C.) | $T_i$ (° C.) | $\Delta H_m$ (J/g) | $\Delta H_i$ (J/g) | LC phase |
|---|---|---|---|---|---|
| Example 7 | 191 | 295 | 16.96 | 35.12 | Nematic |
| Example 8 | 255 | 313 | 16.76 | 82.42 | Nematic |
| Example 9 | 215 | 284 | 18.32 | 45.36 | Nematic |
| Example 10 | 218 | 275 | 25.36 | 56.23 | Nematic |
| Example 11 | 263 | 295 | 32.01 | 74.14 | Nematic |

Example 12

Synthesis of Liquid Crystal Thermoset ("LCT") Oligomer 3.3 g (0.03 mol) of 4-aminophenol, 3.7 g (0.02 mol) of 4,4-dihydroxybiphenyl and 18 ml of triethylamine were dissolved in 100 ml of DMF in a 250 ml flask. The solution was cooled to 0-5° C. and 8.6 g (0.0425 mol) of isophthaloyl chloride was added thereto. The mixture was allowed to react at room temperature for 2 hours. To the reaction mixture was added 3.8 g (0.015 mol) of the methylmaleimido-benzoyl chloride synthesized in Preparative Example 1. The resulting mixture was allowed to react for 10 hours. After completion of the reaction, the reaction mixture was poured into water to obtain a precipitate. The precipitate was collected by filtration under reduced pressure, washed sequentially with water and ethanol and dried under vacuum to afford a methylmaleimide-terminated LCT oligomer of Formula 19:

(19)

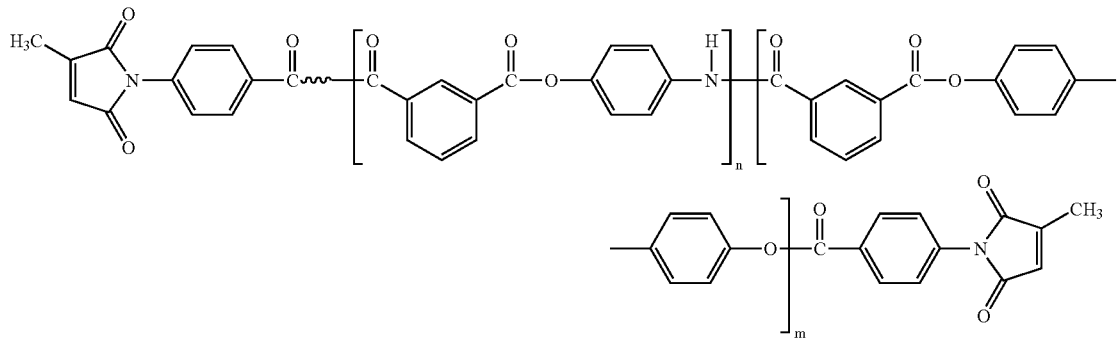

wherein n/m is 3/2.

The LCT oligomer had a number average molecular weight of 2,780, as measured by gel permeation chromatography ("GPC").

Example 13

Synthesis of Liquid Crystal Thermoset Oligomer

A methylmaleimide-terminated LCT oligomer was prepared in the same manner as in Example 12 except that the amounts of 4-aminophenol and 4,4-dihydroxybiphenyl added were changed to 3.8 g (0.035 mol) and 2.8 g (0.015 mol), respectively. The LCT oligomer had a number average molecular weight of 2,950, as measured by gel permeation chromatography ("GPC").

Example 14

Synthesis of Liquid Crystal Thermoset Oligomer

A dimethylmaleimide-terminated LCT oligomer of Formula 20 was prepared in the same manner as in Example 12 except that 4.0 g (0.015 mol) of the dimethylmaleimido-benzoyl chloride synthesized in Preparative Example 2 was used instead of methylmaleimido-benzoyl chloride.

(20)

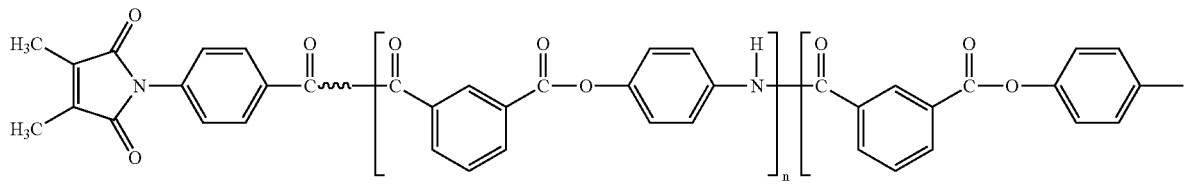

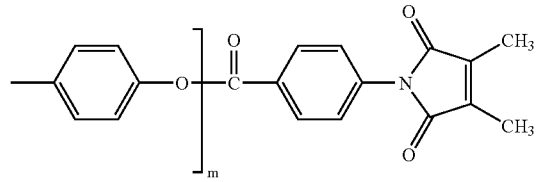

wherein n/m is 3/2.

The LCT oligomer had a number average molecular weight of 2,730, as measured by gel permeation chromatography ("GPC").

Preparative Example 3

Synthesis of Nadimido-benzoyl Chloride

Nadimido-benzoyl chloride was synthesized in the same manner as in Preparative Example 1 except that 49.2 g (0.3 mol) of 5-nobornene-2,3-dicarboxylic anhydride was used instead of 33.6 g (0.3 mol) of citraconic anhydride.

Preparative Example 4

Synthesis of Methylnadimido-benzoyl Chloride

Methylnadimido-benzoyl chloride was synthesized in the same manner as in Preparative Example 1 except that 53.5 g (0.3 mol) of methyl-5-norbornene-2,3-dicarboxylic anhydride was used instead of 33.6 g (0.3 mol) of citraconic anhydride.

Preparative Example 5

Synthesis of Maleimido-benzoyl Chloride

Maleimido-benzoyl chloride was synthesized in the same manner as in Preparative Example 1 except that 29.4 g (0.3 mol) of maleic anhydride was used instead of 33.6 g (0.3 mol) of citraconic anhydride.

Comparative Example 1

Synthesis of Liquid Crystal Thermoset ("LCT") Monomer

The bisnadimide compound of Formula 21 was synthesized in the same manner as in Example 1 except that 9.1 g (0.03 mol) of the nadimido-benzoyl chloride synthesized in Preparative Example 3 and 1.6 g (0.015 mol) of hydroquinone were used.

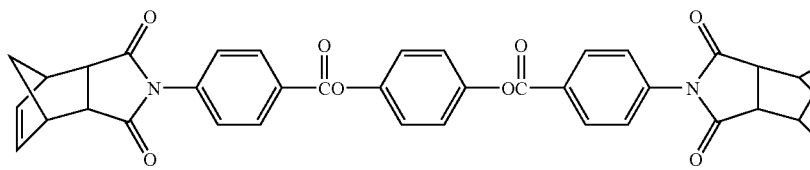

(21)

The results of DSC and liquid crystallinity analyses for the product are summarized in Table 3 below.

Comparative Example 2

Synthesis of Liquid Crystal Thermoset ("LCT") Monomer

The bisnadimide compound of Formula 22 was synthesized in the same manner as in Example 1 except that 9.1 g (0.03 mol) of the nadimido-benzoyl chloride synthesized in Preparative Example 3 and 2.8 g (0.015 mol) of 4,4'-biphenol were used.

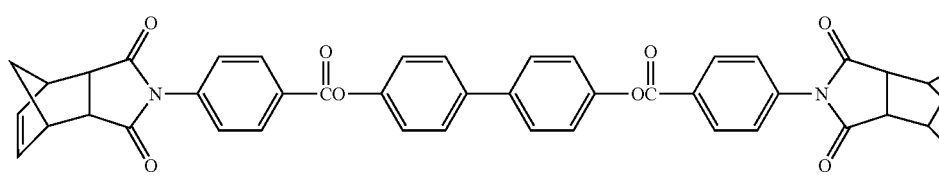

(22)

Figure 13:
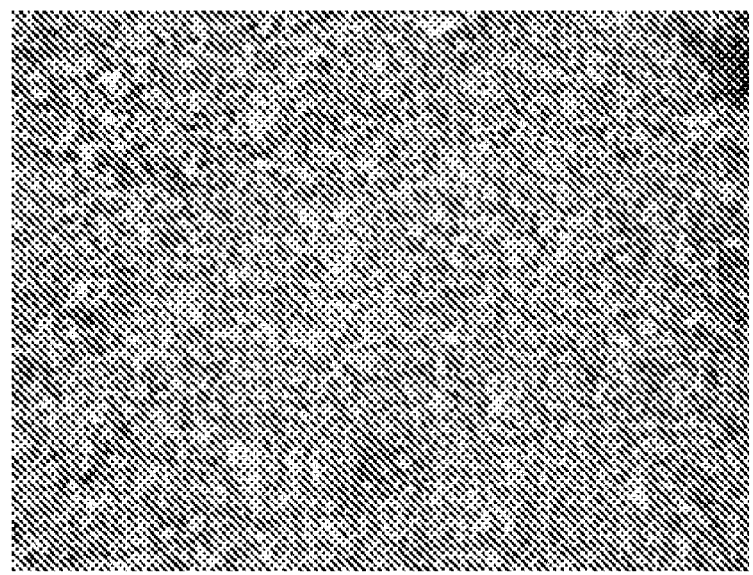
FIG. 13 is an optical micrograph showing the liquid crystal phase of a compound synthesized in Comparative Example 2.

The thermal properties and the liquid crystallinity of the product were evaluated by the methods described in Example 1. FIG. 13 is an optical micrograph (magnification: 250×) showing the liquid crystal phase of the product at 325° C. The micrograph reveals that the liquid crystal phase was nematic. The results of DSC and liquid crystallinity analyses are summarized in Table 3.

Comparative Example 3

Synthesis of Liquid Crystal Thermoset ("LCT") Monomer

The bisnadimide compound of Formula 23 was synthesized in the same manner as in Example 1 except that 9.1 g (0.03 mol) of the nadimido-benzoyl chloride synthesized in Preparative Example 3 and 2.4 g (0.015 mol) of 2,6-dihydroxynaphthalene were used.

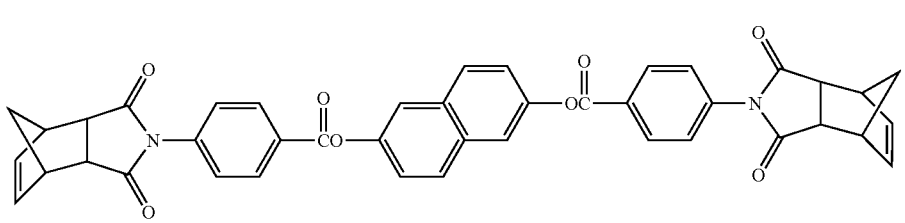

(23)

The thermal properties and the liquid crystallinity of the product were evaluated by the methods described in Example 1. The results of DSC and liquid crystallinity analyses are summarized in Table 3.

TABLE 3

|  | $T_m$ (° C.) | $T_i$ (° C.) | $\Delta H_m$ (J/g) | $\Delta H_i$ (J/g) | LC phase |
| --- | --- | --- | --- | --- | --- |
| Comparative Example 1 | 308 | 349 | 78.90 | 1.15 | Nematic |
| Comparative Example 2 | 275 | 354 | 19.13 | 98.08 | Nematic |
| Comparative Example 3 | 245 | 320 | — | 64.33 | Nematic |

Although the nadimide-terminated liquid crystal thermoset monomers showed nematic liquid crystallinity, they suffer from the disadvantages that their curing temperatures (280-350° C.) are too high to be used for the production of printed circuit boards and cyclopentadiene bubbles formed during curing may damage the surfaces of prepregs and films.

Comparative Example 4

Synthesis of Liquid Crystal Thermoset ("LCT") Monomer

The bis(methylnadimide) compound of Formula 24 was synthesized in the same manner as in Example 1 except that 10.1 g (0.032 mol) of the methylnadimido-benzoyl chloride synthesized in Preparative Example 4 and 1.7 g (0.016 mol) of hydroquinone were used.

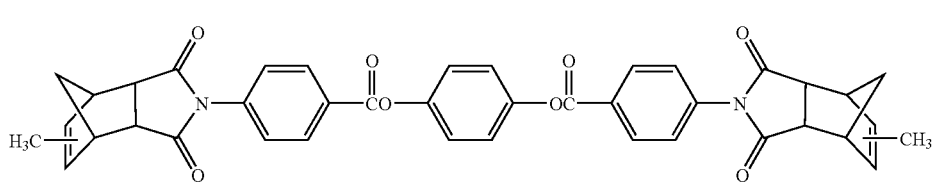

(24)

The thermal properties and the liquid crystallinity of the product were evaluated by the methods described in Example 1. The results of DSC and liquid crystallinity analyses are summarized in Table 4 below.

Comparative Example 5

Synthesis of Liquid Crystal Thermoset ("LCT") Monomer

The bis(methylnadimide) compound of Formula 25 was synthesized in the same manner as in Example 1 except that 10.1 g (0.032 mol) of the methylnadimido-benzoyl chloride synthesized in Preparative Example 4 and 2.98 g (0.016 mol) of 4,4'-biphenol were used.

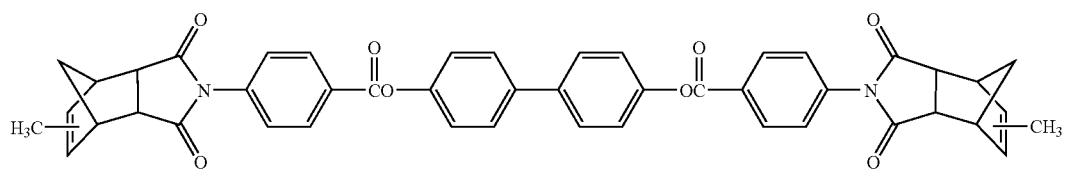

(25)

The thermal properties and the liquid crystallinity of the product were evaluated by the methods described in Example 1. The results of DSC and liquid crystallinity analyses are summarized in Table 4 below.

Comparative Example 6

Synthesis of Liquid Crystal Thermoset ("LCT") Monomer

The bis(methylnadimide) compound of Formula 26 was synthesized in the same manner as in Example 1 except that 10.1 g (0.032 mol) of the methylnadimido-benzoyl chloride synthesized in Preparative Example 4 and 2.5 g (0.016 mol) of 2,6-dihydroxynaphthalene were used.

TABLE 4

| | $T_m$ (° C.) | $T_i$ (° C.) | $\Delta H_m$ (J/g) | $\Delta H_i$ (J/g) | LC phase |
|---|---|---|---|---|---|
| Comparative Example 4 | 224 | — | 78.90 | — | Not observed |

TABLE 4-continued

| | $T_m$ (° C.) | $T_i$ (° C.) | $\Delta H_m$ (J/g) | $\Delta H_i$ (J/g) | LC phase |
|---|---|---|---|---|---|
| Comparative Example 5 | 232 | — | 19.13 | — | Not observed |
| Comparative Example 6 | 320 | — | 64.33 | — | Not observed |

Comparative Example 7

Synthesis of Liquid Crystal Thermoset ("LCT") Monomer

The bismaleimide compound of Formula 27 was synthesized in the same manner as in Example 1 except that 9.5 g (0.04 mol) of the maleimido-benzoyl chloride synthesized in Preparative Example 5 and 2.1 g (0.02 mol) of hydroquinone were used.

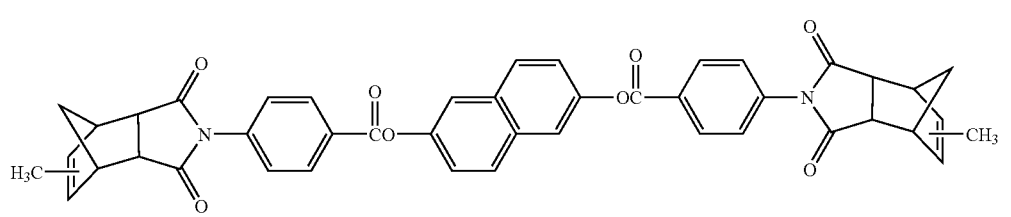

(26)

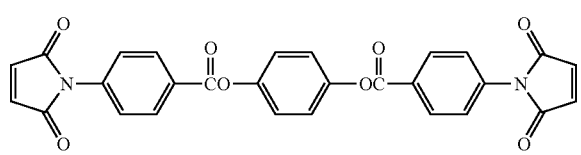

(27)

The thermal properties and the liquid crystallinity of the product were evaluated by the methods described in Example 1. The results of DSC and liquid crystallinity analyses are summarized in Table 5 below.

Comparative Example 8

Synthesis of Liquid Crystal Thermoset ("LCT") Monomer

The bismaleimide compound of Formula 28 was synthesized in the same manner as in Example 1 except that 9.5 g (0.04 mol) of the maleimido-benzoyl chloride synthesized in Preparative Example 5 and 3.7 g (0.02 mol) of 4,4'-biphenol were used.

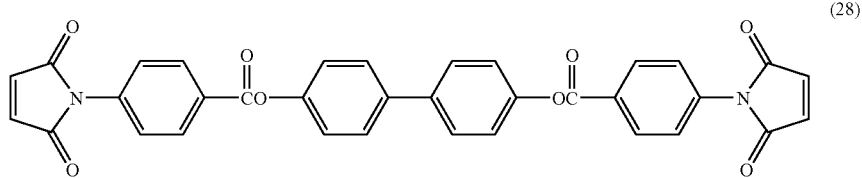

(28)

The thermal properties and the liquid crystallinity of the product were evaluated by the methods described in Example 1. The results of DSC and liquid crystallinity analyses are summarized in Table 5 below.

Comparative Example 9

Synthesis of Liquid Crystal Thermoset ("LCT") Monomer

The bismaleimide compound of Formula 29 was synthesized in the same manner as in Example 1 except that 9.5 g (0.04 mol) of the maleimido-benzoyl chloride synthesized in Preparative Example 5 and 3.2 g (0.02 mol) of 2,6-dihydroxynaphthalene were used.

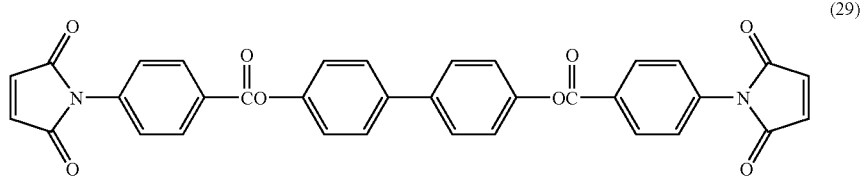

(29)

The thermal properties and the liquid crystallinity of the product were evaluated by the methods described in Example 1. The results of DSC and liquid crystallinity analyses are summarized in Table 5.

TABLE 5

| | $T_m$ (° C.) | $T_i$ (° C.) | $\Delta H_m$ (J/g) | $\Delta H_i$ (J/g) | LC phase |
|---|---|---|---|---|---|
| Comparative Example 7 | 275 | — | 45.18 | — | Not observed |
| Comparative Example 8 | 217 | — | 8.24 | — | Not observed |

TABLE 5-continued

| | $T_m$ (° C.) | $T_i$ (° C.) | $\Delta H_m$ (J/g) | $\Delta H_i$ (J/g) | LC phase |
|---|---|---|---|---|---|
| Comparative Example 9 | 220 | — | 38.66 | — | Not observed |

As can be seen from the results in Tables 4 and 5, the methylnadimide-terminated LCT monomers and maleimide-terminated LCT monomers did not show nematic liquid crystallinity. This is thought to be because the melting points of the LCT monomers overlap the crosslinking temperatures of maleimide or methylnadimide, leading to a deterioration in the ability to form liquid crystals.

Example 15

Figure 5:
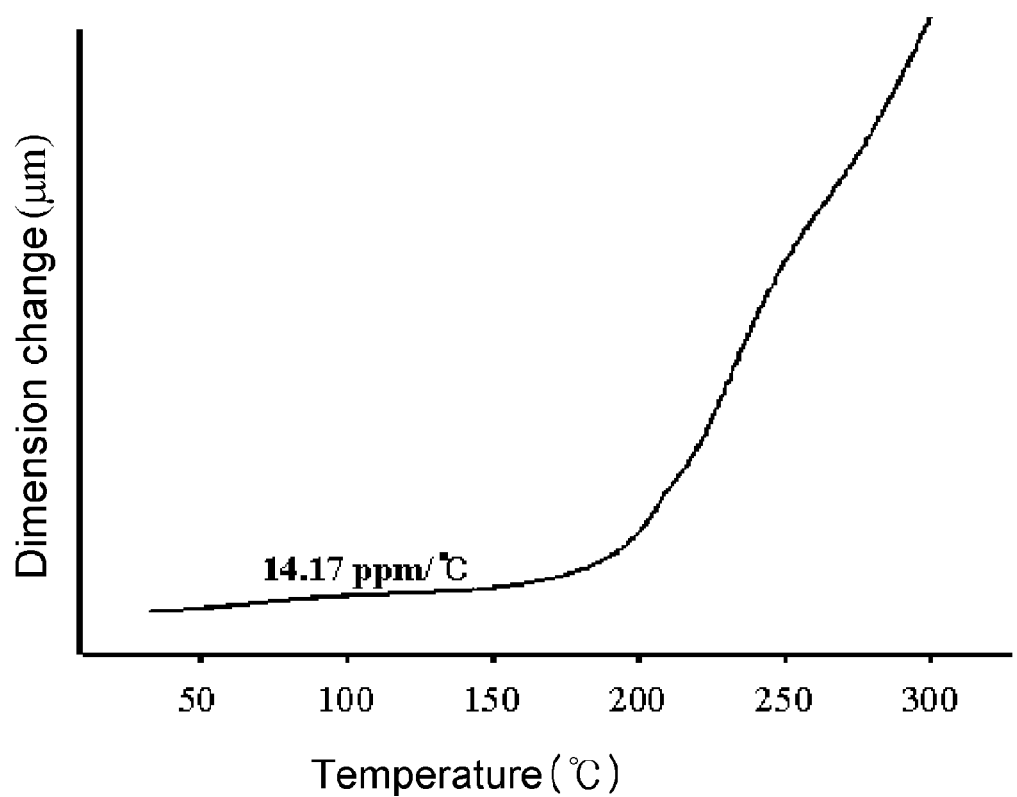
FIG. 5 is a graph showing the results of thermomechanical analysis ("TMA") for a film produced in Example 15.

Production of LCT Film 2 g of the bis(methylmaleimide) compound synthesized in Example 1 was dissolved in 8 g of N-methyl-2-pyrrolidone ("NMP"). The LCT solution was coated on a glass plate (10×10 cm²), heated on a hot plate at 120° C. for 20 minutes, baked in a vacuum oven at 180° C. for one hour and at 350° C. for 30 minutes, followed by curing. The glass plate coated with the cured film was dipped in an aqueous hydrofluoric acid solution (2 wt %) to peel the cured film. The film was cut to an appropriate size and annealed at 150° C. for 60 minutes. The coefficient of thermal expansion ("CTE") of the annealed film was measured by thermomechanical analysis ("TMA"), (TMA 2940, TA Instruments). The CTE measurement was performed under a nitrogen atmosphere while raising the temperature at a rate of 5° C./min. FIG. 5 shows a TMA curve for the cured film. The CTE of the cured film was found to be 14.17 ppm/° C. in the temperature range of 50-150° C.

Example 16

Production of LCT Film

Figure 6:
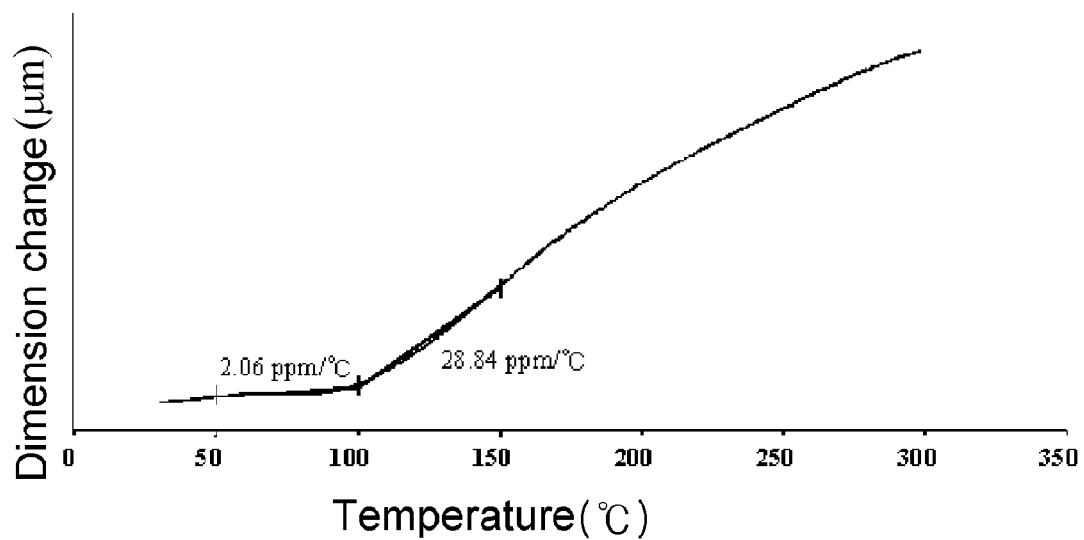
FIG. 6 is a graph showing the results of TMA for a film produced in Example 16.

A film was produced in the same manner as in Example 15 except that the bis(methylmaleimide) compound synthesized in Example 2 was used. FIG. 6 shows a TMA curve for the cured film. The CTE of the cured film was found to be 2.06 ppm/° C. in the temperature range of 50-100° C.

Example 17

Figure 7:
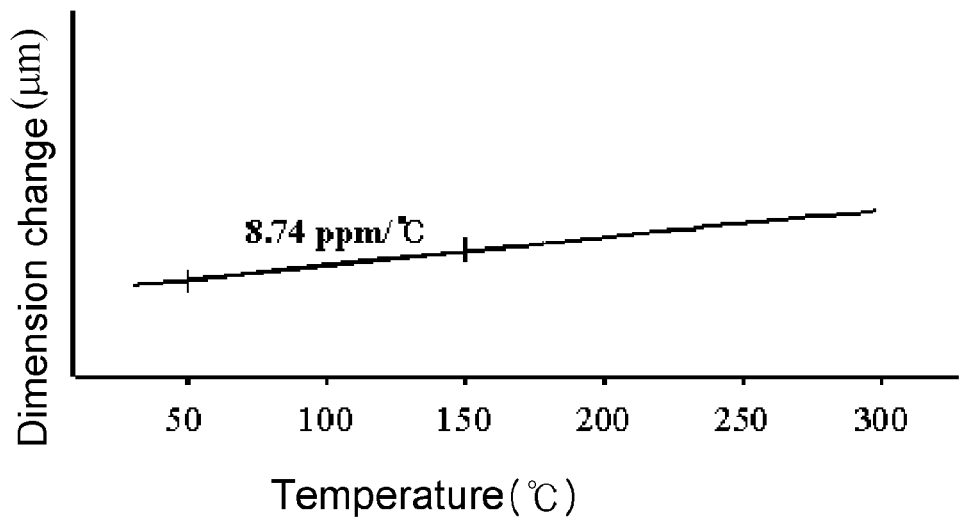
FIG. 7 is a graph showing the results of TMA for a prepreg produced in Example 17.

Production of Prepreg 3 g of the bis(methylmaleimide) compound synthesized in Example 1 was dissolved in 7 g of N-methyl-2-pyrrolidone ("NMP"). The LCT solution was impregnated into a glass fiber having a thickness of 0.05 mm and a size of 4×4 cm$^2$. The sample was placed on an electrodeposited copper foil and dried in an electric furnace for one hour while raising the temperature from room temperature to 300° C. The specimen was treated with 50 parts by weight of an aqueous nitric acid solution to completely remove the copper foil, leaving a prepreg only. At this time, 0.5 parts by weight of the polymer was impregnated into one part by weight of the glass fiber. FIG. 7 shows a TMA curve for the cured prepreg. The CTE of the cured prepreg was found to be 8.74 ppm/° C. in the temperature range of 50-150° C. The curve shows that the prepreg produced using the methylmaleimide compound is suitable for use as a material for a printed circuit board.

Example 18

Figure 8:
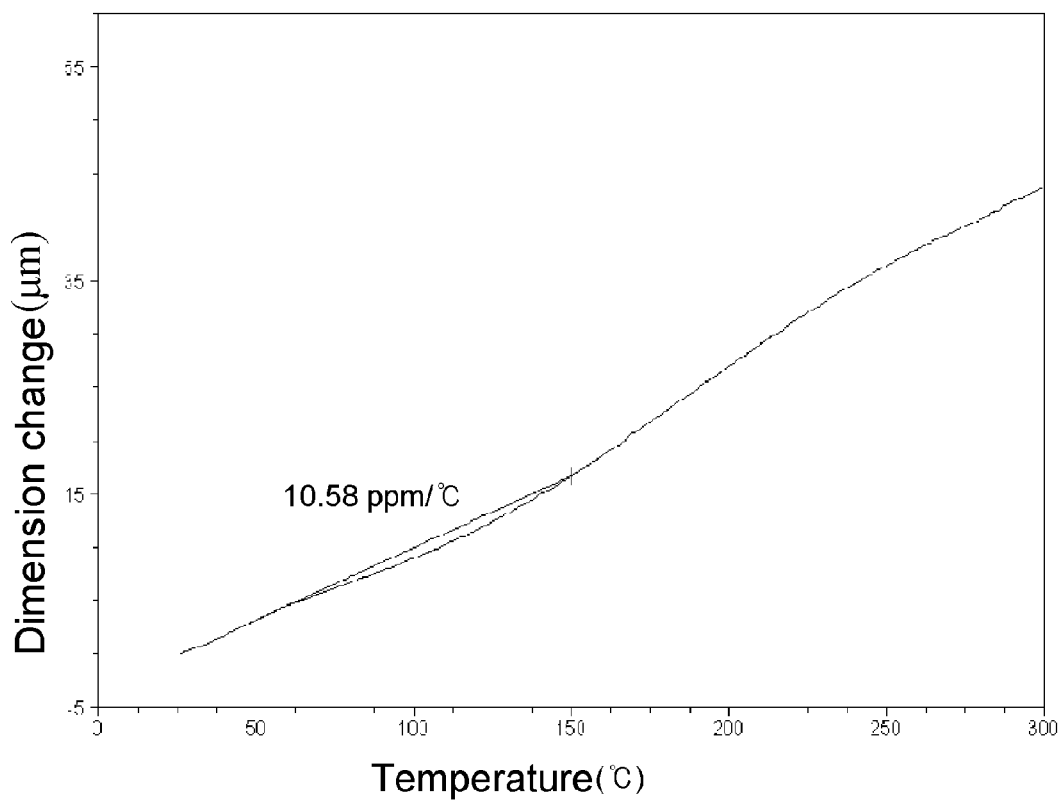
FIG. 8 is a graph showing the results of TMA for a prepreg produced in Example 18.

Production of Prepreg 1.4 g of poly(amide-ester) ($M_n$=15,000) as a soluble liquid crystal polymer and 0.6 g of the bis(methylmaleimide) compound synthesized in Example 2 were dissolved in 8 g of NMP. The LCT solution was impregnated into a glass fiber and cured in accordance with the procedure described in Example 17 to produce a prepreg. At this time, 0.54 parts by weight of the polymer was impregnated into one part by weight of the glass fiber. The CTE of the cured prepreg was found to be 9.9 ppm/° C. in the temperature range of 100-150° C. FIG. 8 shows a TMA curve for the cured prepreg. The curve shows that the prepreg produced using the soluble liquid crystal polymer and the methylmaleimide compound is suitable for use as a material for a printed circuit board.

Example 19

Production of Prepreg 3 g of the LCT oligomer synthesized in Example 12 was dissolved in 7 g of NMP. The LCT solution was impregnated into a glass fiber and cured in accordance with the procedure described in Example 17 to produce a prepreg. The results of TMA for the prepreg are summarized in Table 6 below.

Example 20

Production of Prepreg 3 g of the LCT oligomer synthesized in Example 13 was dissolved in 7 g of NMP. The LCT solution was impregnated into a glass fiber and cured in accordance with the procedure described in Example 17 to produce a prepreg. The results of TMA for the prepreg are summarized in Table 6 below.

Example 21

Production of Prepreg 3 g of the LCT oligomer synthesized in Example 14 was dissolved in 7 g of NMP. The LCT solution was impregnated into a glass fiber and cured in accordance with the procedure described in Example 17 to produce a prepreg. The results of TMA for the prepreg are summarized in Table 6.

TABLE 6

|  | Example 19 | Example 20 | Example 21 |
|---|---|---|---|
| Glass transition temperature ($T_g$, ° C.) | 178 | 171 | 189 |
| Coefficient of thermal expansion (CTE, ppm/° C.) | 8.5 | 9.5 | 8.2 |

The results in Table 6 show that each of the prepregs produced using the methylmaleimide-terminated LCT oligomers had a coefficient of thermal expansion ("CTE") not greater than 10 ppm/° C. and can provide good flexibility to printed circuit boards. In conclusion, the above disclosed LCT monomer or oligomer terminated with methylmaleimide can be used to produce a board material with excellent mechanical and thermal properties. In addition, the board material is easy to handle. Therefore, the prepregs are suitable for use as materials for printed circuit boards and the use of the board material allows for the production of a high-performance printed circuit board.

Although exemplary embodiments have been described herein with reference to the foregoing preferred embodiments, those skilled in the art will appreciate that various modifications and changes are possible without departing from the spirit of the invention as disclosed in the accompanying claims. Therefore, it is to be understood that such modifications and changes are encompassed within the scope of the present invention.

What is claimed is:

1. A liquid crystal thermoset (LCT) monomer or oligomer having both ends capped with maleimide having at least one methyl group, represented by Formula 1:

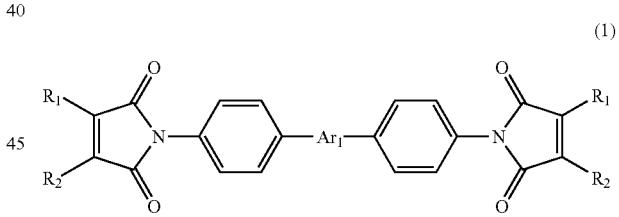

(1)

wherein $R_1$ and $R_2$ are each independently $CH_3$ or H, and at least one of $R_1$ and $R_2$ is a methyl group, and $Ar_1$ is a divalent organic group containing one or more structural units selected from the group consisting of ester, amide, ester amide, ester imide and ether imide units, and $Ar_1$ has a molecular weight not greater than 5,000.

2. The LCT monomer or oligomer of claim 1, wherein $Ar_1$ contains one or more structural units selected from the group consisting of the following units 2:

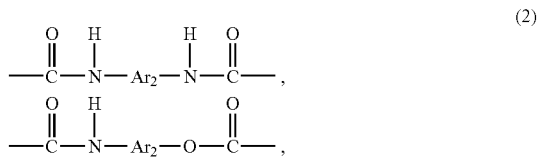

(2)

-continued

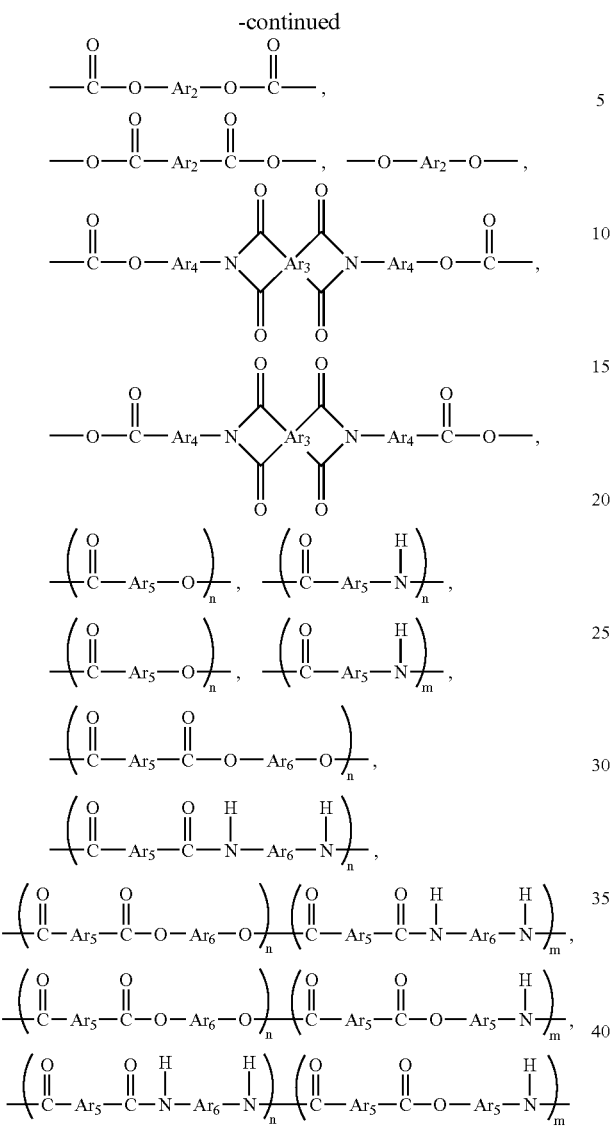

wherein Ar$_2$, Ar$_4$, Ar$_5$ and Ar$_6$ are each independently a divalent aromatic organic group containing one or more structural units selected from the group consisting of the following units 3:

(3)

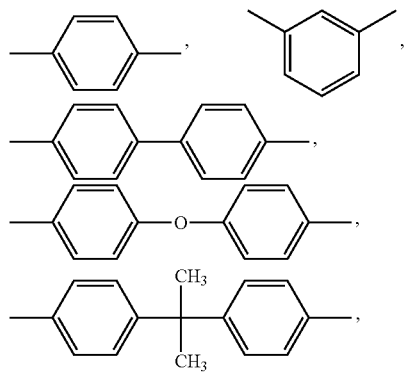

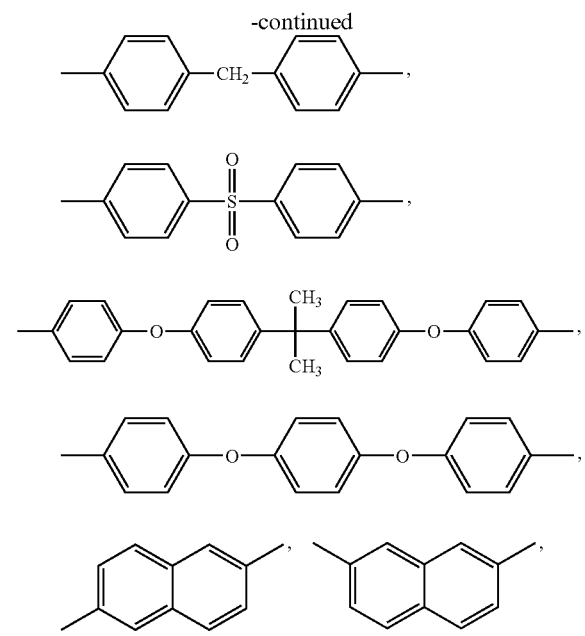

each Ar$_3$ is a tetravalent aromatic organic group containing one or more structural units selected from the group consisting of the following units 4:

(4)

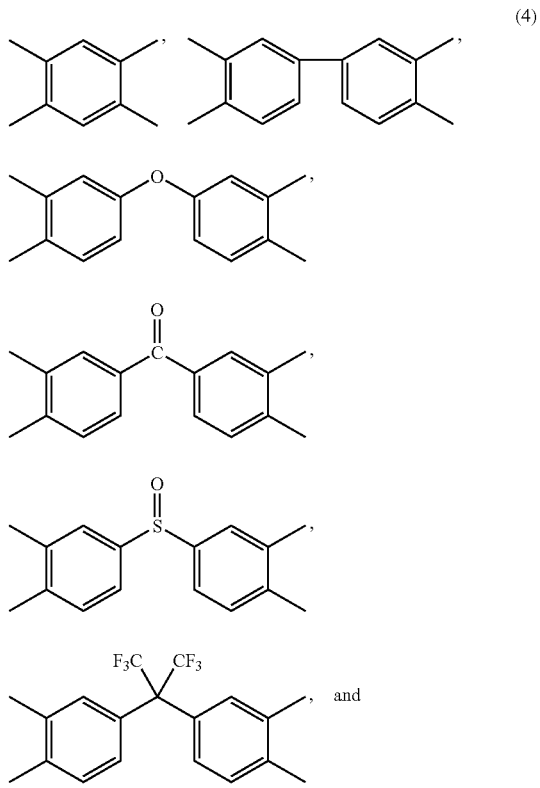

n and m are each independently an integer from 1 to 100.

3. The LCT monomer or oligomer of claim 1, wherein the LCT monomer or oligomer is selected from the following compounds of Formulae 5 to 20:

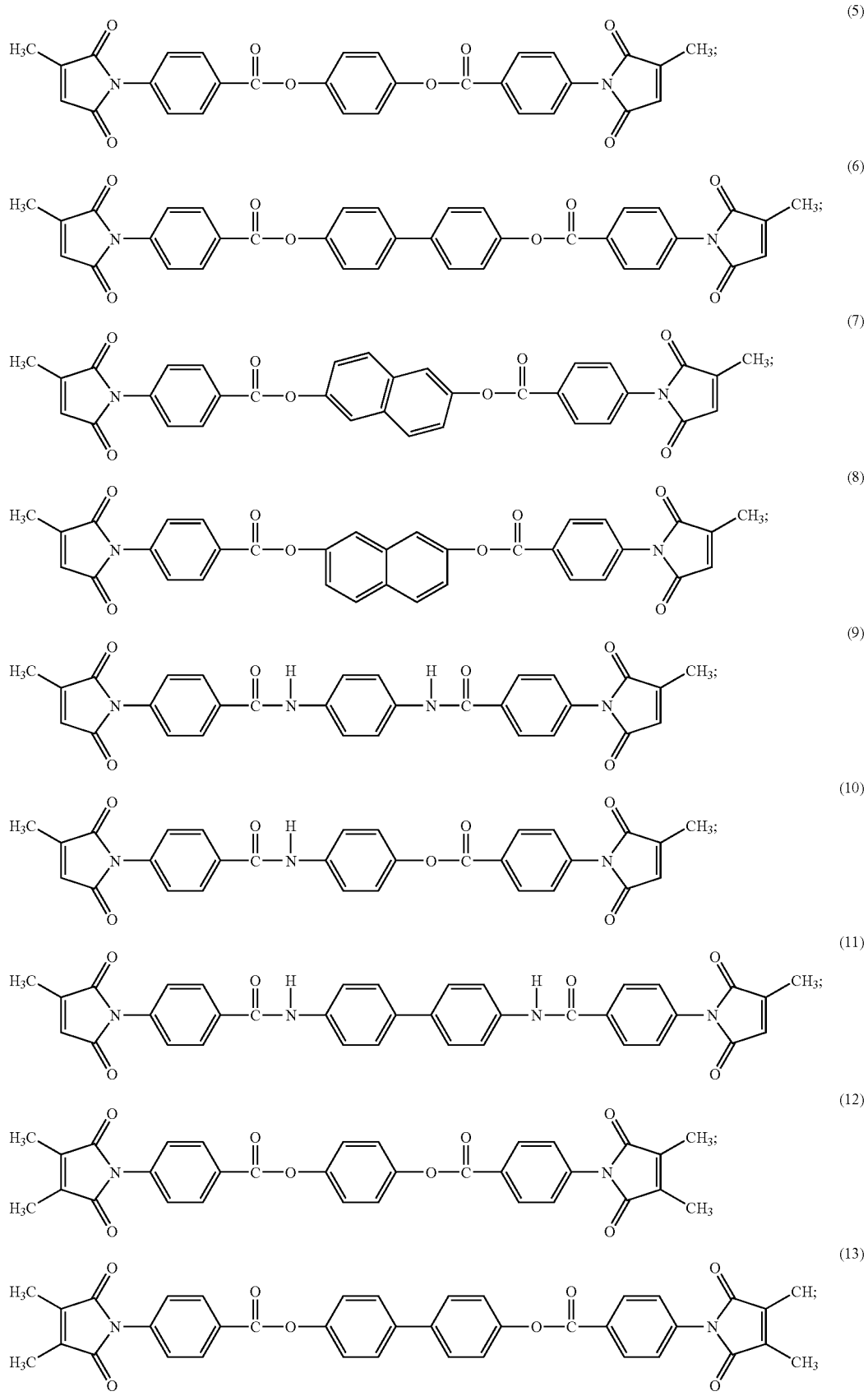

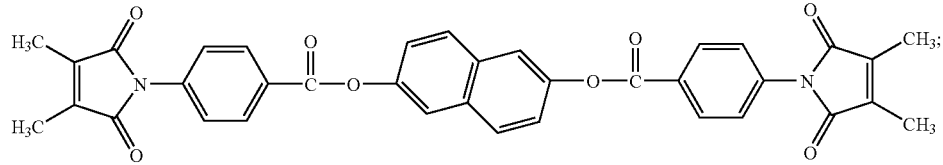
(14)
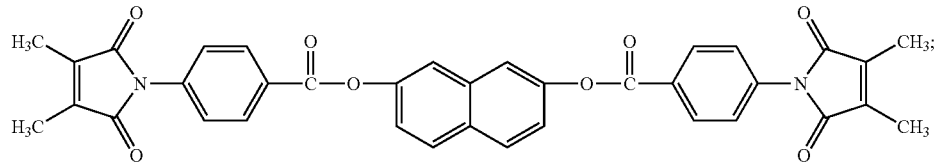
(15)
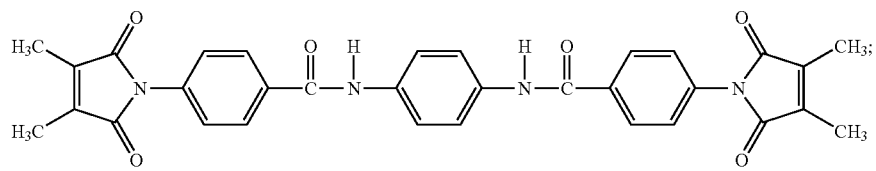
(16)
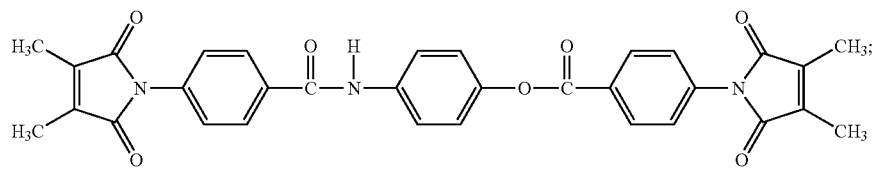
(17)
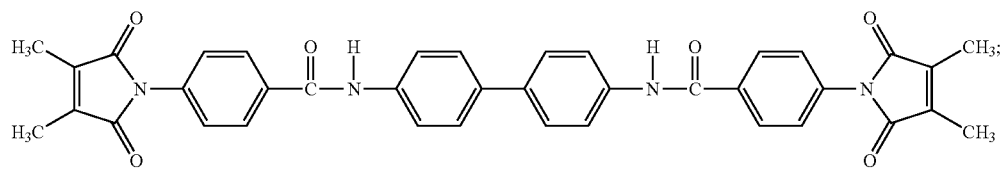
(18)
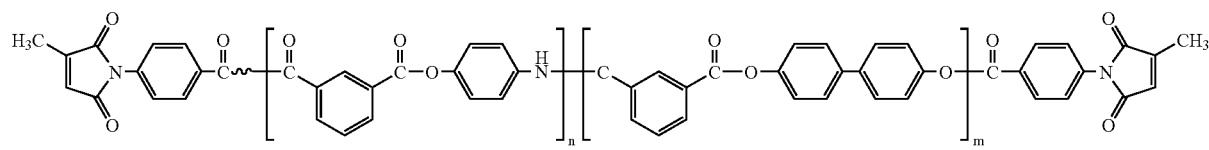
(19)
wherein m and n are each independently an integer from 1 to 30; and
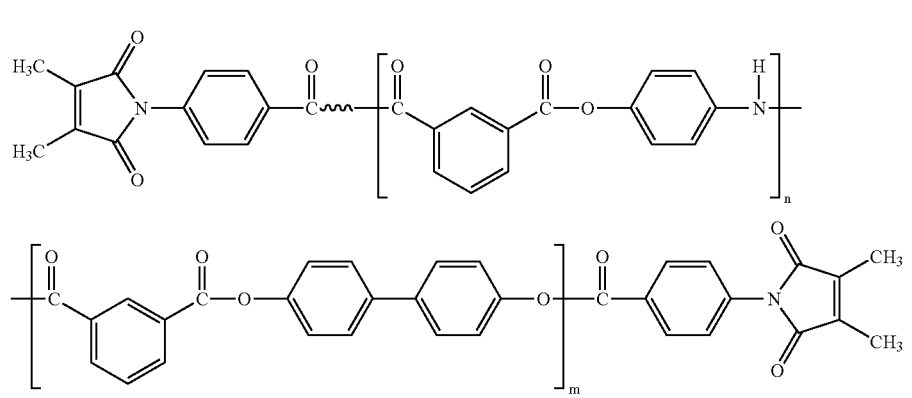
(20)

wherein m and n are each independently an integer from 1 to 30.

4. The LCT monomer or oligomer of claim 1, wherein the LCT monomer or oligomer has a molecular weight in the range of 300 to 5,000.

5. A thermosetting liquid crystal polymer (LCP) composition comprising a liquid crystal thermoset (LCT) monomer or oligomer and a liquid crystal polymer wherein both ends of the LCT monomer or oligomer are capped with maleimide having at least one methyl group, the LCT monomer or oligomer being represented by Formula 1:

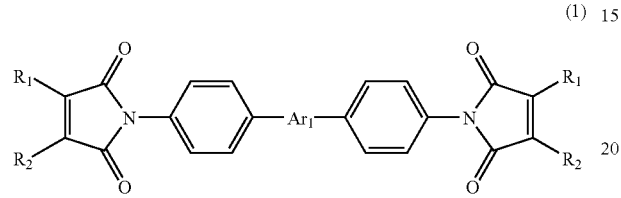

(1)

wherein $R_1$ and $R_2$ are each independently $CH_3$ or H, with the proviso that at least one of $R_1$ and $R_2$ is a methyl group, and $Ar_1$ is a divalent organic group containing one or more structural units selected from the group consisting of ester, amide, ester amide, ester imide and ether imide units and having a molecular weight not greater than 5,000.

6. The composition of claim 5, wherein $Ar_1$ contains one or more structural units selected from the group consisting of the following units 2:

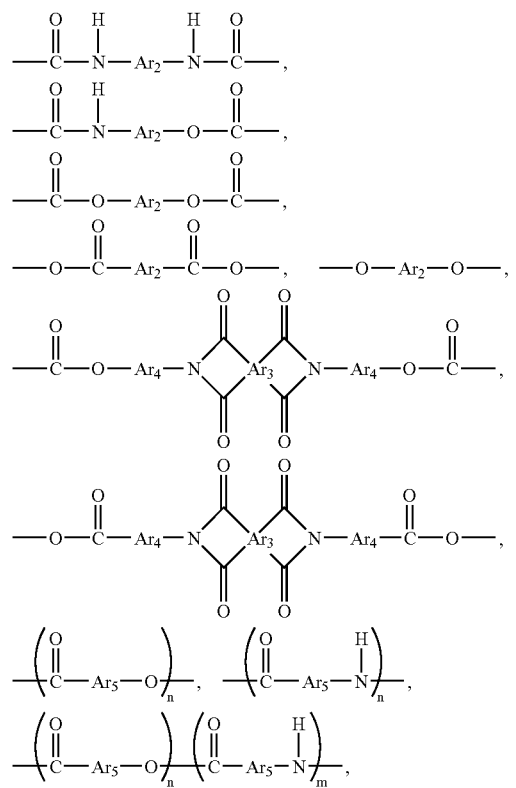

(2)

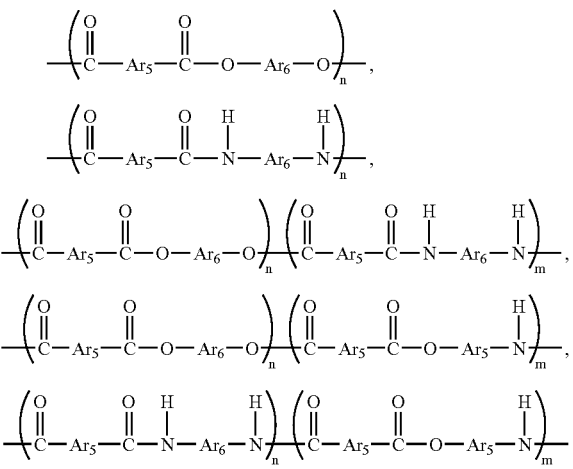

-continued

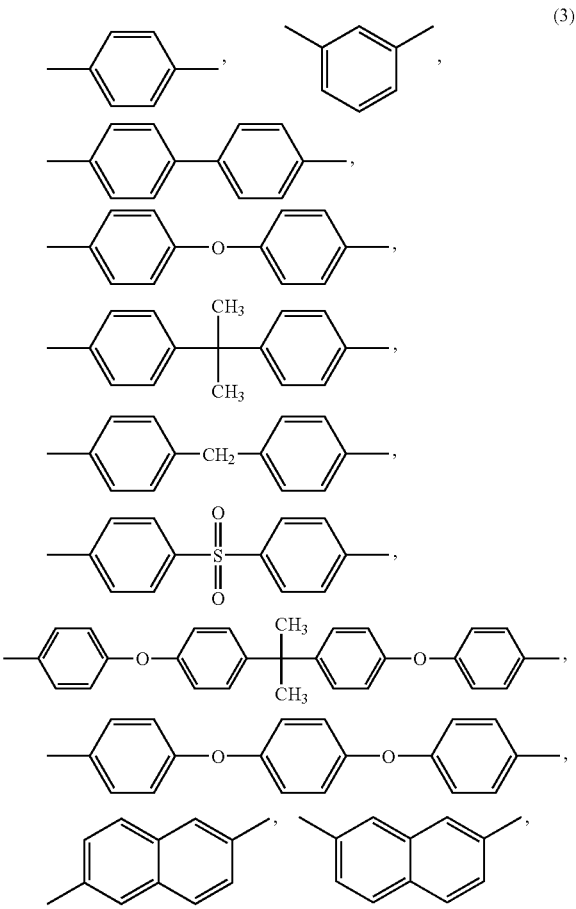

wherein $Ar_2$, $Ar_4$, $Ar_5$ and $Ar_6$ are each independently a divalent aromatic organic group containing one or more structural units selected from the group consisting of the following units 3:

(3)

each $Ar_3$ is a tetravalent aromatic organic group containing one or more structural units selected from the group consisting of the following units 4:

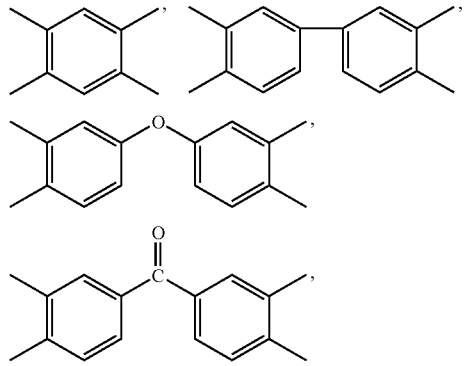
(4)
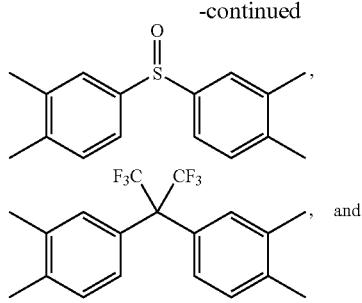
5
10
, and
15 n and m are each independently an integer from 1 to 100.
7. The composition of claim 5, wherein the LCT monomer or oligomer is selected from the group consisting of the following compounds of Formulae 5 to 20:
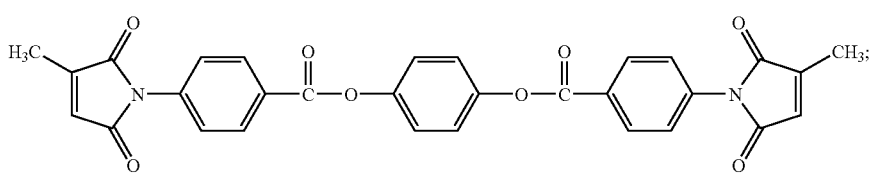
(5)
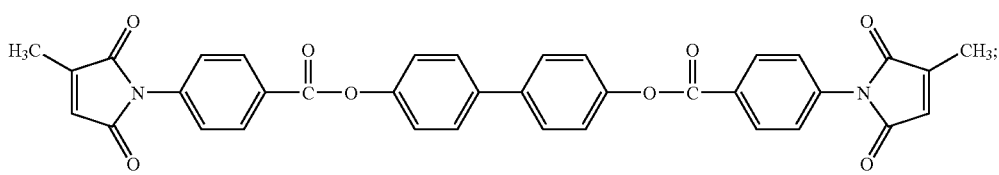
(6)
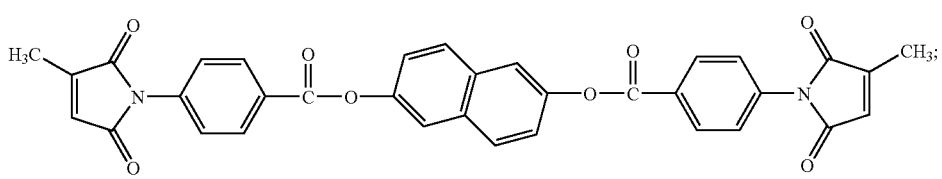
(7)
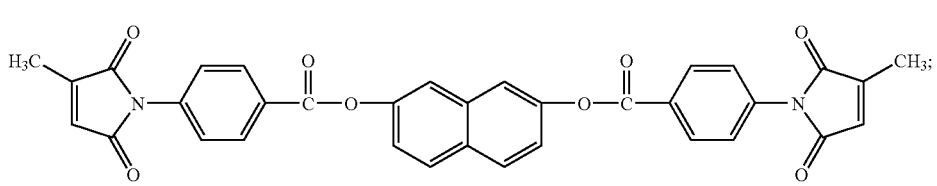
(8)
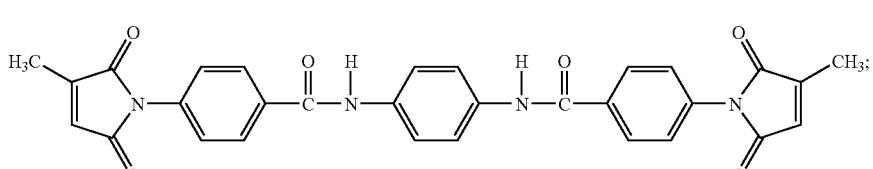
(9)
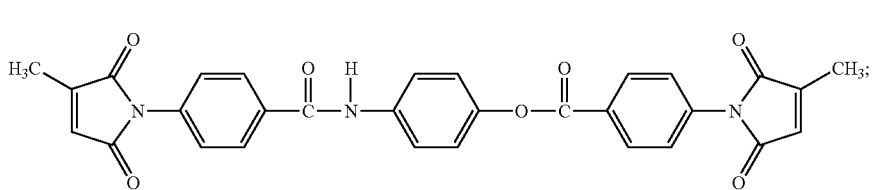
(10)

-continued
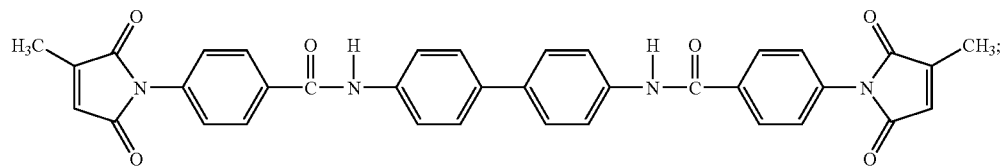
(11)
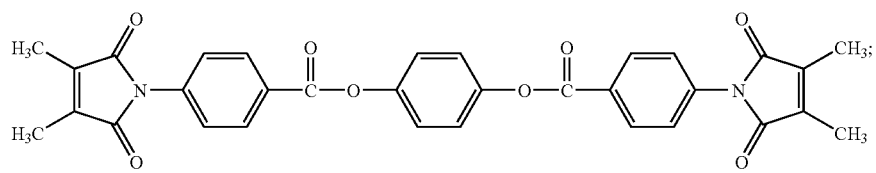
(12)
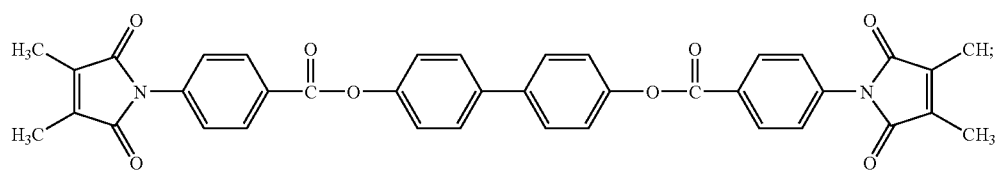
(13)
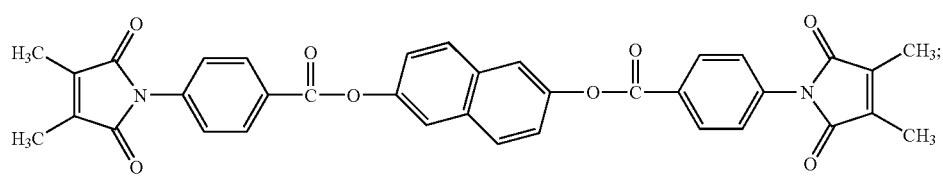
(14)
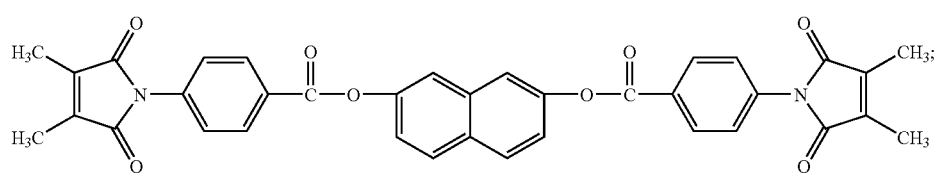
(15)
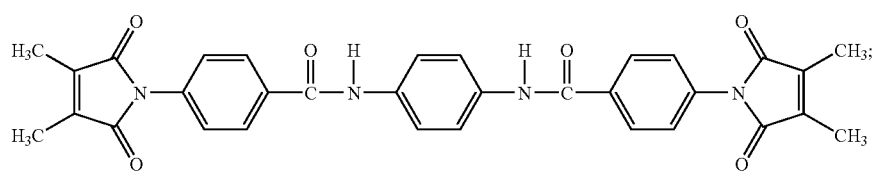
(16)
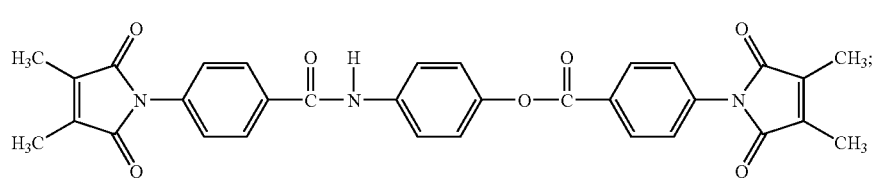
(17)
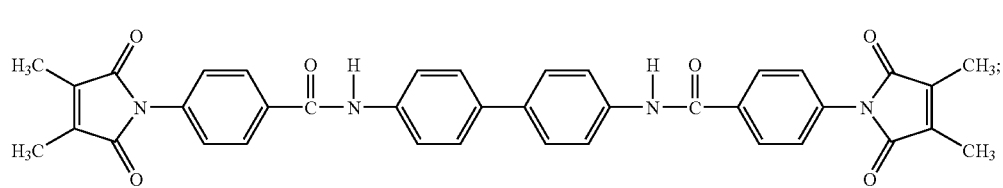
(18)

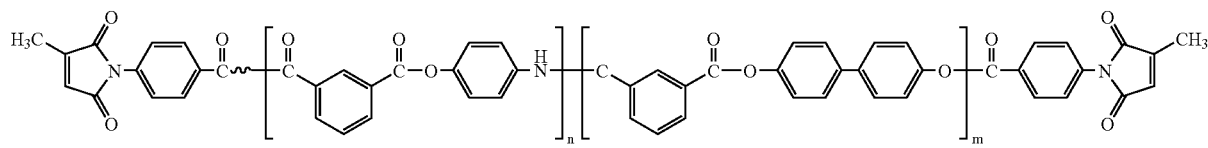

(19)

wherein m and n are each independently an integer from 1 to 30; and

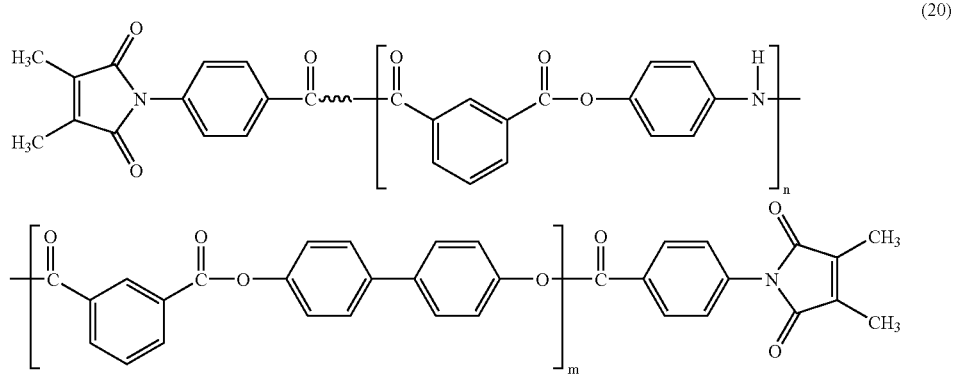

(20)

wherein m and n are each independently an integer from 1 to 30.

8. The composition of claim 5, wherein the LCT monomer or oligomer has a molecular weight in the range of 300 to 5,000.

9. The composition of claim 5, wherein the liquid crystal polymer contains at least one structural unit selected from the following units 1, 2, 3 and 4:

   (1)

wherein $Ar_1$ is 1,4-phenylene, 2,6-naphthylene or 4,4-biphenylene;

   (2)

wherein $Ar_2$ is 1,4-phenylene, 1,3-phenylene or 2,6-naphthylene;

   (3)

wherein X is NH, $Ar_3$ is 1,4-phenylene or 1,3-phenylene, and Y is O or NH; and

   (4)

wherein $Ar_4$ is 1,4-phenylene or 1,3-phenylene.

10. The composition of claim 5, wherein the liquid crystal polymer has a molecular weight in the range of 5,000 to 500,000.

11. The composition of claim 5, wherein the composition comprises 5 to 80 parts by weight of the liquid crystal polymer and 20 to 95 parts by weight of the LCT monomer or oligomer.

12. The composition of claim 5, further comprising an aprotic solvent.

13. The composition of claim 5, wherein the LCT monomer or oligomer is soluble in the aprotic solvent.

14. The composition of claim 12, wherein the composition has a solids content not lower than 25 parts by weight, based on 100 parts by weight of the solvent.

15. An article produced using the LCT monomer or oligomer of claim 1.

16. The article of claim 15, wherein the article is a film, a sheet, a composite material or a board.

17. The article of claim 16, wherein the board is a printed board, a copper foil, a copper clad laminate or a prepreg.

* * * * *